United States Patent
Westphal et al.

(10) Patent No.: US 10,272,102 B2
(45) Date of Patent: *Apr. 30, 2019

(54) HYDROXYALKYL STARCH FOR THE TREATMENT OF HEMATOLOGICAL NEOPLASMS

(71) Applicant: FRESENIUS KABI DEUTSCHLAND GMBH, Bad Homburg (DE)

(72) Inventors: Martin Westphal, Bad Homburg (DE); Silke Baasner, Schöneck (DE)

(73) Assignee: FRESENIUS KABI DEUTSCHLAND GMBH, Bad Homburg (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/909,284

(22) PCT Filed: Jul. 29, 2014

(86) PCT No.: PCT/EP2014/066299
§ 371 (c)(1),
(2) Date: Feb. 1, 2016

(87) PCT Pub. No.: WO2015/014851
PCT Pub. Date: Feb. 5, 2015

(65) Prior Publication Data
US 2016/0175341 A1  Jun. 23, 2016

(30) Foreign Application Priority Data

Jul. 30, 2013 (EP) .................. 13003776

(51) Int. Cl.
*A61K 31/718* (2006.01)
*A61K 45/06* (2006.01)
*A61K 31/255* (2006.01)
*A61K 31/395* (2006.01)

(52) U.S. Cl.
CPC .......... *A61K 31/718* (2013.01); *A61K 31/255* (2013.01); *A61K 31/395* (2013.01); *A61K 45/06* (2013.01)

(58) Field of Classification Search
CPC .... A61K 45/06; A61K 31/255; A61K 31/395; A61K 31/718; A61K 2300/00
USPC ........................................... 514/60
See application file for complete search history.

(56) References Cited

U.S. PATENT DOCUMENTS

| 6,207,654 B1 | 3/2001 | Zikria et al. | |
| 8,263,065 B2* | 9/2012 | Hariri | A61K 35/50 424/93.1 |
| 2012/0316137 A1* | 12/2012 | Huang | A61K 31/5025 514/81 |

FOREIGN PATENT DOCUMENTS

| DE | 4023789 A1 | 1/1992 |
| WO | 2010/096466 | 8/2010 |
| WO | 2013/113747 | 8/2013 |

OTHER PUBLICATIONS

Schumann, DE 4023788 A1; English Translation, pp. 1-9.*
Trisha Gura, Science, Nov. 1997, 279(5340), 1041-42.*
Schumann, K. DE 4023788 A1, 1992, English Translation, pp. 1-9.*

* cited by examiner

*Primary Examiner* — Ganapathy Krishnan
(74) *Attorney, Agent, or Firm* — Hylton-Rodic Law PLLC

(57) ABSTRACT

The present invention relates to hydroxyalkyl starch or a pharmaceutical preparation thereof for the treatment of a hematological neoplasm, especially by effectively reducing proliferation rate of cancer cells and inhibiting cancer cell growth and wherein the hydroxyalkyl starch has a mean molecular weight (MW) above 20 and below 1300 kDa and a molar substitution (MS) in the range of from 0.1 to 1.5, wherein the alkylation may be an ethylation, propylation or butylation or mixes thereof; and wherein the alkyl may be further substituted.

16 Claims, 6 Drawing Sheets

HYDROXYALKYL STARCH FOR THE TREATMENT OF HEMATOLOGICAL NEOPLASMS

CROSS-REFERENCE TO RELATED APPLICATIONS

This application is a U.S. national phase application filed under 35 USC § 371 of International Application No. PCT/EP2014/066299, which was filed Jul. 29, 2014, and which claims the benefit of the filing date of EP Application No. 13003776.5, which was filed Jul. 30, 2013. The content of these earlier filed applications is hereby incorporated by reference herein in its entirety.

Cancer, tumor-associated diseases and neoplastic disease states are serious and often life-threatening conditions. A subgroup of cancer types are hematological neoplasms, which are cancer types affecting the blood, bone marrow, and lymphoid system.

Most types of cancer affecting the blood or bone marrow are called leukemia (American English) or leukaemia (British English). They are characterized by an abnormal increase of immature white blood cells called "blasts". The term leukemia comprises most hematological neoplastic diseases of the blood or bone marrow, for example, myelogenic (or myeloid) leukemia, besides the lymphoma. The term lymphoma refers to a group of hematological neoplasms, which develop from lymphocytes, such as Hodgkin lymphoma (HL) and non-Hodgkin lymphoma (NHL).

Most leukemia treatments involve chemotherapy, medical radiation therapy, hormone treatments, or bone marrow transplantation. The rate of cure depends on the type of leukemia as well as the age of the patient. In the year 2000 approximately 256,000 children and adults around the world developed some form of leukemia, and 209,000 died from it. About 90% of all leukemia is diagnosed in adults.

The hematological neoplasms affecting the lymphoid system are called lymphoma. Lymphoma is a type of cancer that occurs, for example, when B or T lymphocytes, divide faster than normal cells or have an extended life span. Lymphoma may develop in the lymph nodes, spleen, bone marrow, blood or other organs and eventually they may form a tumor. It is hardly possible to diagnose lymphoma before a tumor has started to grow, but the detection of malignant highly proliferative cells in the lymphoid system is possible. Accordingly a treatment of lymphoma may not only target the reduction of tumor growth, and/or tumor cell growth but also the rate of proliferation of these cells.

If lymphoma cells accumulate in lymph nodes, they may form a tumor which is presenting as an enlargement of the node. These cells can also affect other organs and form tumors there in which case the neoplasm is referred to as extranodal lymphoma. Extranodal sites include the skin, brain, bowels and bone. The central nervous system lymphoma is a rare non-Hodgkin lymphoma type in which malignant (cancer) cells from lymph tissue accumulate in the brain and/or the spinal cord (primary CNS) or spread from other parts of the body to the brain and/or spinal cord (secondary CNS).

Another type of hematological neoplasms is the lymphoid leukemia, which also originates in lymphocytes but typically involves only circulating blood and the bone marrow and sites with extramedullary hematopoiesis (where blood cells are generated in a process termed hematopoiesis) and does not usually form static solid tumors.

Lymphoma treatment might involve chemotherapy and in some cases radiotherapy and/or bone marrow transplantation.

The latest classification by the WHO (2008) lists many different forms of lymphoma and leukemia divided into four broad groups (Swerdlow, Steven H.; International Agency for Research on Cancer; World Health Organization (2008). *WHO classification of tumours of haematopoietic and lymphoid tissues.* World Health Organization classification of tumors 2 (4th ed.). International Agency for Research on Cancer.). This system attempts to group lymphomas and leukemia by cell type (i.e. the normal cell type that most resembles the cancer) and defining phenotypic, molecular or cytogenetic characteristics. There are three large groups: the B cell, T cell, and natural killer cell tumors. Other less common groups, are also recognized. Hodgkin lymphoma, although considered separately within the World Health Organization (and preceding) classifications, is now recognized as being a tumor of, albeit markedly abnormal, lymphocytes of mature B cell lineage.

In the following the term hematological neoplasms is understood to encompass all forms of cancer types that are affecting the blood, bone marrow, and lymphoid system, preferably leukemia and lymphoma. It is to be understood that the group of hematological neoplasms does not comprise angiosarcoma though which are cancers of endothelial-type cells that line vessel walls. This may be in reference to blood (hemangiosarcoma) or lymphatic vessels (lymphangiosarcoma).

The hematological neoplasms, which are characterized by uncontrolled cell proliferation, are also a focal point of many research projects, devoted to identifying new active therapeutic ingredients which prove to be effective in the treatment of these diseases. Such active ingredients prolong the life expectancy of the patient, inhibit the rapidly progressing cell growth associated with the haematological neoplasm, or bring about regression of the hematological neoplasm, or improve the quality of life of afflicted patients.

Currently, the routine treatment of hematological diseases, such as leukemia and lymphoma, relies on three treatment options, surgery, radiation therapy and chemotherapy. Therefore a large number of patients diagnosed with haematological diseases are currently treated with chemotherapy.

Chemotherapy is a term that is used to describe the administration of drugs, which are designed to kill highly proliferating cells, such as cancer cells, or tumor cells, or at least to stop them from proliferating any further. These drugs are commonly referred to as cytostatic or cytotoxic drugs. These drugs however are not selective in killing only the cancer cells. Hence this type of treatment is associated with severe side effects for the patient.

A non-comprehensive list of potential side effects comprises anemia, nausea, vomiting, appetite changes, diarrhea, constipation, fatigue, pain, hair loss, bleeding, swelling, increased susceptibility for infection, reduced memory, nerve changes, mouth and throat changes, sexual and fertility changes, skin and nail, urination problems. These side effects can be so severe, that the treatment with cytostatica has to be stopped due to the high toxicity, in order to keep the patient alive. However, during these phases of recovery, wherein the patient may regain some general health, the tumor often also recovers and starts to grow again. The problem of the high toxicity of cytostatica is well known. Hence there is a need in the art for a treatment option for patients, being afflicted with hematological neoplasms, which inhibits progression of cancer while not stressing or impairing the subject in need of treatment any further.

An ideal cancer treatment would target the tumor growth and the tumor cell proliferation selectively. Healthy cell proliferation at a normal and controlled rate would be unaffected.

Hydroxyalkyl starches (HAS) are polymers which are derived from natural base materials and are modified. HAS are prepared from amylopectin-rich starches. The parent starch may be branched or unbranched, or may consist of a mixture of both. Hydroxyethyl starches are based almost exclusively on amylopectin, in other words on branched chains of glucose molecules.

Hydroxyalkyl starch, and more particularly hydroxyethyl starch, is used in volume therapy as a plasma substitute, and also in clinical haemodialysis (Sommermeyer et al., 1987, Krankenhauspharmazie, 8(8): 271-278; Weidler et al., 1991, Arzneimittelforschung/Drug Research, 41: 494-498). A hydroxyethyl starch solution, which allows the erythrocytes (red blood corpuscles) to continue transporting oxygen through the body, may be administered intravenously, in order to prevent a state of shock following severe blood loss caused by trauma or by surgery.

Additionally it has been proposed to use the colloid-osmotic properties of HES solutions to extend the exposure time of chemotherapeutic drugs, when these are applied locally. In some treatment regimens of peritoneal carcinomatosis the cytotoxic or cytostatic drugs of the chemotherapy are applied locally into the peritoneum. Here the local use of solutions containing HES in addition to the pharmaceutical ingredient results in higher retention times of the cytotoxic or cytostatic drug in the peritoneum, compared to the use of dialysis solutions that are free of osmotically active colloids (Mohamed et al (2003) European Journal of Surgical Oncology vol 29, p 261-265).

In WO 96/40108 it has also been suggested to use HES as an absorbable barrier as an anti-adhesion agent in injured body cavities.

The current invention provides hydroxyalkylated starch for use in treating hematological neoplasms and especially for use in any of the methods described below. It further provides methods of treating hematological neoplasms.

The method of treatment comprises administering to a subject diagnosed with a hematological neoplasm a hydroxyalkylated starch and thereby effectively reducing tumor growth rate, reducing cancer cell growth, reducing the proliferation rate of the cancer cells, reducing the proliferative activity or reducing the number of cancer cells in the subject, wherein the cancer cells are originating from the hematological neoplasm, or caused by the hematological neoplasm. Preferably this is achieved while at the same time no toxic side effects, or significantly less toxic side effects, will occur than with a standard treatment with cytostatica.

The invention also comprises a kit providing for two substances in different compartments, a cytostatic or cytotoxic composition, preferably the standard-of-care drug, in one compartment, for example in a first vial, and the HAS, preferably as injectable solution in a second compartment, for example, in a second vial, both presented in one kit.

Another aspect of the invention are pharmaceutical compositions comprising a hydroxyalkylated starch as only therapeutically active ingredient for use in the treatment of hematological neoplasms, for the reduction of tumor growth rate, number of cancer cells, cancer cell growth, proliferation rate of the cancer cells, cancer cell division, or proliferative activity of cancer cells in the subject, wherein the cancer is a hematological neoplasms.

DETAILED DESCRIPTION OF THE INVENTION

While HAS solutions have been administered to a high number of humans (without tumors) without showing any severe side effect, it was now for the first time noticed that these substances might have an anti-proliferative effect on cells which are characteristic for hematological neoplasms. It could be shown in mouse model that tumors derived from subcutaneous application of myelogenic leukemia cells did develop less rapidly than control treated tumors.

Whilst hydroxyalkylated starches have been proposed as stabilizing agents or solubilisers or osmotically active ingredients, it has never been shown that the application of HAS itself has an additional anti-proliferative effect on hematological neoplasms.

According to the invention a hydroxyalkylated starch is provided as therapeutically active compound for use in treating hematological neoplasms, preferably for reducing the tumor growth rate, the number of highly proliferating cells, the number of cancer cells, for reducing the frequency of cancer cell division or for reducing cancer cell growth rates, wherein the cancer is a hematological neoplasm.

Preferably the hydroxyalkylated starch is used for reducing the tumor growth rate, number of cancer cells, proliferation rate of cancer cells, cell growth, cancer cell division, or the proliferative activity of cancer cells wherein the cancer is hematological neoplasm, preferably in a subject diagnosed with a hematological neoplasm. Preferably the treatment is not affecting a normally proliferating cell.

In a further embodiment the invention relates to methods of treatment of hematological neoplasms comprising the administration of hydroxyalkylated starch according to the invention.

The method of treatment comprises administering to a subject a first compound, comprising or consisting of a hydroxyalkylated starch, that is effective in at least one of reducing tumor growth rate, reducing cancer cell growth, reducing the proliferation rate of the cancer cells, reducing the proliferative activity or reducing the number of cancer cells in the subject.

Preferably the method comprises the following steps: In a first step the hydroxyalkylated starch is administered and in a second step a second compound selected from the group consisting of cytostatica, biologicals with anti-cancer activity and hormones with anti-cancer activity is administered. The first step may be performed prior to the second step or after the second step. The administration of the second compound may be performed according to a doctor's routine treatment, for example, at the same amount of active ingredient, and/or at the same frequency as it would be given in standard therapy, or it may be performed with reduced amounts and reduced frequency according to the patient's needs. Preferably the method of treatment involves administration of lesser amounts of the second compound, preferably with lesser amounts of cytostatica than when given as only treatment option.

In a preferred embodiment of the treatment method the hydroxyalkylated starch is administered to a subject prior to the beginning of a treatment regimen with, or prior to the administration of the second compound.

It is a preferred embodiment according to the invention that the administration of HAS or of a pharmaceutical composition comprising HAS is repeated (administration of boluses) according to the requirements of the patient diagnosed with hematological neoplasm, who either thereafter or before or simultaneously receives a standard therapy based on administration of one or more compounds selected from the group consisting of cytostatica, biologicals with anti-cancer activity and hormones with anti-cancer activity.

The group consisting of cytostatica, biologicals with anti-cancer activity and hormones with anti-cancer activity is meant to comprise all the drugs that are commonly given to a patient suffering from a leukemia or lymphoma type. Especially, the term cytostatica is meant to describe a group of drugs comprising, or preferably consisting of alkylating agents, alkyl sulfonates, antimetabolites, anti-tumor antibiotics, topoisomerase inhibitors, mitotic inhibitors, proteasom inhibitors, small molecule tyrosine kinase inhibitors, differentiating agents, immunomodulating drugs and Plerixafor. The group of cytostatica comprises

- alkylating agents, comprising nitrogen mustard types like cyclophosphamide to treat ALL and myeloma, lymphomas, leukemia, multiple myeloma, chlorambucil used to treat lymphomas, CLL and Hodgkin's Lymphoma, bendamustine used to treat CLL and lymphomas, ifosfamide to treat non-Hodgkin's Lymphoma, mechlorethamine to treat fungoides-type cutaneous T-cell lymphoma (CTCL), melphalam used to treat multiple myeloma; and nitrosoureas, such as carmustine to treat multiple myeloma, Hodgkin's disease and Non-Hodgkin's lymphomas, lomustine to treat Hodgkin Lymphoma; and triazines, such as dacarbazine to treat metastatic malignant melanoma, and Hodgkin and Non-Hodgkin lymphoma, and benzamides, such as procarbazine used to treat lymphomas, and cisplatin;
- alkyl sulfonates, comprising busulfan used to treat CML;
- antimetabolites, comprising 6-mercaptopurine used to treat leukemia, ALL and pediatric non-Hodgkin's lymphoma, clofarabine, a purine nucleoside antimetabolite used to treat relapsed or refractory ALL, cytarabine used to treat ALL, AML, non-Hodgkin's Lymphoma, CML and meningeal leukemia, methotrexate, a dihydrofolate reductase inhibitor used to treat lymphomas and leukemia, thioguanine, a purine analog used to treat acute lymphoblastic leukemia, especially in children, nelarabine, another purine nucleoside analog used to treat T-Cell ALL, T-Cell lymphoblastic lymphoma, cladribine used to treat hairy cell leukemia, fludarabine used to treat CLL, indolent non-Hodgkin's lymphomas and AML, pentostatin used to treat hairy cell leukemia, hydroxyurea used to treat myeloproliferative disease, gemcitabine used to treat lymphoma, pralatrexate, used to treat relapsed or refractory peripheral T-cell lymphoma, nelarabine used to treat T-cell ALL and T-cell lymphoblastic lymphoma;
- anti-tumor antibiotics, comprising anthracyclines, such as daunorubicin used to treat ALL and AML, and doxorubicin used to treat ALL and AML and different types of leukemia and lymphomas and idarubicin used to treat AML, ALL and CML; and bleomycin to treat Hodgkin's lymphoma and other lymphoma;
- topoisomerase inhibitors, comprising teniposide used to treat ALL and etoposide used to treat Hodgkin's and non-Hodgkin's lymphoma, and non-lymphocytic leukemia, mitoxantrone used to treat AML and non-Hodgkin's lymphoma;
- mitotic inhibitors, comprising vincristine used to treat ALL acute leukaemia, malignant lymphoma, Hodgkin's disease and acute erythraemia, vinblastine used to treat Hodgkin's and non-Hodgkin's lymphomas, ixabepilone used to treat non-Hodgkin's lymphoma;
- proteasome inhibitors, comprising bortezomib used to treat relapsed multiple myeloma and mantle cell lymphoma and carfilzomib used to treat multiple myeloma;
- tyrosine kinase inhibitors, comprising imatinib to treat the Philadelphia chromosome positive chronic myeloid leukemia, Ph+ acute lymphoblastic leukemia and CML, dasatinib to treat adults with Philadelphia chromosome-positive acute lymphoblastic leukemia with resistance or intolerance to prior therapy and CML, and ponatinib to treat Philadelphia chromosome positive acute lymphoblastic leukemia, CML; such as ibrutinib used to treat CLL and lymphomas, bosutinib used to treat Philadelphia chromosome-positive (Ph+) CML and nilotinib to treat imatinib-resistant CML;
- differentiating agents, comprising tretinoin used to treat acute promyelocytic leukemia, bexarotene used to treat cutaneous T cell lymphoma, and arsenic trioxide used to treat acute promyelocytic leukemia;
- immunomodulating drugs comprising thalidomide and lenalidomide used to treat multiple myeloma, and pomalidomide used to treat anti-angiogenic relapsed and refractory multiple myeloma;
- plerixafor to treat lymphoma and multiple myeloma The term biologicals with anti-cancer activity is meant to describe a group of drugs comprising, or preferably consisting of antibody tyrosine kinase inhibitors, differentiating agents, monoclonal antibodies, immunomodulating drugs.

The group of biologicals with anti-cancer activity according to the invention comprises

- antibody tyrosine kinase inhibitors, comprising e.g. cetuximab, bevacizumab, panitumumab, and trastuzumab;
- monoclonal antibodies, comprising e.g. rituximab used to treat CD20-positive non-Hodgkins lymphoma and chronic lymphocytic leukemia, alemtuzumab used to treat B-cell chronic lymphocytic leukemia, ofatumumab used to treat CLL, Follicular non-Hodgkin's lymphoma or diffuse large B-cell lymphoma, obinutuzumab used to treat CLL and to kill B-cells, and brentuximab vedotin to treat Hodgkin lymphoma and systemic anaplastic large cell lymphoma, and siltuximab to treat multiple myeloma;
- immunomodulating proteins comprising e.g. antibodies such as belimumab used to treat systemic lupus erythematodes, canakinumab used to treat CAPS syndromes, infliximab used to treat Morbus Crohn, ipilimumab used to treat melanoma and natalizumab used to treat multiple sclerosis.

The hormones with anti-cancer activity comprise melatonin and corticosteroids. The corticosteroids comprise prednisone or prednisolone, which is used in the treatment of ALL and non-Hodgkin's lymphoma, Hodgkin's lymphoma and multiple myeloma, and dexamethasone, which is used in the treatment of multiple myeloma.

Other adjuvant therapies may also be combined with a treatment based on administration of HAS as therapeutically active compound.

In a preferred embodiment of the method of treatment a hydroxyalkylated starch is administered repeatedly during treatment intervals, while the patient recovers from the side effects of having been treated with the second compound.

In another preferred embodiment the therapeutically effective substance according to the invention is administered continuously while the patient either thereafter or before or within the time of continuous administration receives a standard therapy based on administration of one or more compounds selected from the group consisting of cytostatica, biologicals with anti-cancer activity and hormones with anti-cancer activity.

Preferably, a simultaneous administration, by administering a single composition comprising both substances, the hydroxyalkylated starch and the compound selected from the group consisting of cytostatica, biologicals with anti-cancer activity and hormones with anti-cancer activity, is not encompassed in the scope of the invention, unless explicitly specified.

In a preferred embodiment the hydroxyalkylated starch and the second compound are not comprised in the same pharmaceutical composition, preferably they are not administered simultaneously.

Preferably the method comprising a first step a) of administering of HAS and prior to or after step a) a second step b) of administering one or more compounds selected from the group consisting of cytostatica, biologicals with anti-cancer activity and hormones with anti-cancer activity, which are given as standard-of-care treatment of hematological neoplasms, is less straining for the patient diagnosed with a hematological neoplasm and causing less side effects than the treatment with one or more compounds selected from the group consisting of cytostatica, biologicals with anti-cancer activity and hormones with anti-cancer activity, which are given as standard-of-care treatment of hematological neoplasms, alone.

In a preferred embodiment the method of treatment according to the invention is more effective than treating the same disease by administration of a compound selected from the group consisting of cytostatica, preferably selected from the group consisting of cytostatica, biologicals with anti-cancer activity and hormones with anti-cancer activity.

In a further embodiment, the invention relates to a kit comprising a pharmaceutical composition comprising HAS according to the invention for the treatment of hematological neoplasms. Preferably the kit comprises also a second pharmaceutical composition comprising one or more therapeutically active compounds selected from the group consisting of cytostatica, biologicals with anti-cancer activity and hormones with anti-cancer activity. Preferably the therapeutically active compound in the second pharmaceutical composition is selected from those approved by the EMEA or FDA for treating leukemia or lymphoma patients, most preferably it is the standard of care drug.

According to the invention, the term "cancer" refers to a proliferative disorder or disease caused or characterized by the proliferation of cells which have lost susceptibility to normal growth control. The term encompasses a disease which is associated with the growing of tumors and any other cell proliferative disorders. The term is meant to include all pathological conditions involving uncontrolled growth of cells, irrespective of stage or of invasiveness.

In one embodiment the cancer may be localized to a specific tissue or organ (e.g. in the breast, the prostate or the lung), and, thus, may not have spread beyond the tissue of origin. In another embodiment the cancer may be invasive, and, thus may have spread beyond the layer of tissue in which it originated into the normal surrounding tissues (frequently also referred to as locally advanced cancer). Invasive cancers may or may not be metastatic. In a preferred embodiment the cancer is metastatic. A cancer is metastatic, if it has spread from its original location to distant parts of the body.

Further the term cancer is understood to describe all types of cancer known in the art.

The term "tumor" is meant to describe a localized accumulation of cells that are growing in an uncontrolled manner, an abnormally grown or growing body tissue, or a localized accumulation of proliferating cells. Tumors can be cancerous (malignant) or noncancerous (benign). A cell proliferative disease emerging from a body tissue results in the occurrence of a solid tumor whereas hematological neoplasms like lymphomas and leukemia emerging from blood, lymphatic or bone marrow cells are considered non-solid malignancies. Leukemia, a type of hematological neoplasms, do not usually form tumors. Lymphomas however may present themselves as tumors. Usually the cells accumulate in the lymph nodes before a subject is diagnosed with lymphoma.

It is generally preferred that the hematological neoplasms are characterized by the absence of solid tumors, due to the preferred treatment wherein the subject is treated before a tumor has formed, or at least before a second tumor has formed, if a first tumor has been diagnosed already. When the definition of a specific hematological neoplasm relies on the appearance or genetic characteristics (markers) of the tumor cells, this tumor is originating from cancer cells floating through the blood or lymphatic system before accumulating to form a tumor. In a preferred treatment the patient is treated before a solid tumor has formed.

However, it is expected that leukemic cells, when injected subcutaneously, cause a tumor to grow locally. That principle is used in an animal model to study the treatment options for leukemia.

A "pharmaceutical composition" according to the invention comprises a therapeutically effective amount of a HAS, as described herein, which can be further substituted, for example via the hydroxyl function attached at the alkyl rest, or instead of this hydroxyl function, and preferably of all those HAS and HES that are specifically and explicitly disclosed, including thio-HAS and thio-HES.

The pharmaceutical composition may comprise solid or liquid formulations of different concentrations. Different embodiments comprising the hydroxyl alkylated starch either on its own or as a pharmaceutical composition are described in more detail below: According to the invention the active ingredient, hydroxyalkyl starch may be administered on its own, simply dissolved in an electrolytic solution, or it may be used in combination with a pharmaceutical excipient. Generally, the hydroxyalkyl starch itself will be in a solid form which can be combined with a suitable pharmaceutical excipient that can be in either solid or liquid form. As excipients carbohydrates, inorganic salts, antimicrobial agents, antioxidants, surfactants, buffers, acids, bases, and combinations thereof may be mentioned. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; and alditols, such as mannitol, maltitol, lactitol, xylitol, sorbitol (glucitol), pyranosyl sorbitol, myoinositol, and the like. The excipient may also include an inorganic salt or buffer such as citric acid, sodium chloride, potassium chloride, sodium sulfate, potassium nitrate, sodium phosphate monobasic, sodium phosphate dibasic, and combinations thereof.

The pharmaceutical composition according to the present invention may also comprise an antimicrobial agent for preventing or determining microbial growth, such as, e.g., benzalkonium chloride, benzethonium chloride, benzyl alcohol, cetylpyridinium chloride, chlorobutanol, phenol, phenylethyl alcohol, phenylmercuric nitrate, thiomersal, and combinations thereof.

The pharmaceutical composition according to the present invention may also comprise an antioxidant, such as, e.g., ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

The pharmaceutical composition according to the present invention may also comprise a surfactant, such as, e.g., polysorbates or sorbitan esters; lipids, such as phospholipids and lecithin and other phosphatidylcholines, phosphatidylethanolamines, acids and fatty esters; steroids, such as cholesterol; and chelating agents, such as EDTA or zinc.

The pharmaceutical composition according to the present invention may also comprise acids or bases such as, e.g., hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof, and/or sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

In a preferred embodiment the pharmaceutical composition, comprises a hydroxyalkyl starch according to the invention as the sole ingredient with therapeutic activity in treating hematological neoplasms, more preferably as the only compound with therapeutic activity in treating cancer, more preferably the only therapeutically active compound approved by the European Medicines Agency (EMA)- or Food and Drug Administration (FDA)-approved drug or both for treating cancer.

Most preferably the HAS is the only pharmaceutically active ingredient in such a pharmaceutical composition, or more preferably the only therapeutically active compound approved from either the European Medicines Agency (EMA)- or the Food and Drug Administration (FDA) or both.

The term "standard-of-care drug" or "standard of care treatment" represents the optimal drug as described for the respective cancer type. In the context of the invention it is used to describe the best available treatment a patient would receive when presented to an oncologist, skilled in the field.

The term "reference drug" represents the optimal drug as described for the respective animal model. In the FIGS. 1 and 2 it has been referred to as "SOC".

The terms "treating or treatment of hematological neoplasms" and "treating or treatment of patients being diagnosed with hematological neoplasms", refer to therapeutic measures, wherein the object is to prevent or to slow down (lessen) an undesired physiological change or disorder, such as the growth, development or spread of a hyperproliferative condition of the lymphatic system, the bone marrow or the blood, such as a cell proliferative disease or a neoplastic disease, the forming of a benign or malignant tumor, or metastases therefrom. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission whether partial or total. Metastatic cancer cells usually arise from a cell type disclosed herein and the major difference from the types disclosed herein is that these cells are now present in a tissue from which the cancer cells did not originally develop. Consequently, if a cancer type or proliferative disease is mentioned the term encompasses its metastatic form.

It is to be understood that a treatment can also mean prolonging survival as compared to expected survival if not receiving treatment. It is to be understood that a treatment can also be understood as prevention of cancer or prevention of tumor growth.

In a preferred embodiment the treatment is effective to reduce the growth rate of tumors arising from metastatic cancers or to prevent the formation of metastasis.

It is particularly envisaged that the term "treatment of hematological neoplasms" according to the invention comprises the administration of a therapeutically effective amount of a hydroxyalkylated starch or a pharmaceutical composition comprising hydroxyalkyl starch as the only therapeutically active ingredient. The therapeutically effective amount is the amount that results in at least one of the effects from the group consisting of reducing the number of cancer cells; reducing the tumor size; (e) preventing the forming of a tumor; inhibiting i.e., slowing to some extent and preferably stopping cancer cell infiltration into peripheral organs; preventing the spread of cancer cells (metastasis); inhibiting i.e., slowing to some extent and preferably stopping tumor metastasis; inhibiting, at least to some extent, tumor growth; reducing cell proliferation rates; reducing the number of proliferative cells and relieving to some extent one or more of the symptoms associated with cancer; attenuating, ameliorating or eliminating the hematological neoplasm, and increasing the quality of life. Whether a particular amount of the hydroxyalkylated starch exerts at least one or several of these effects i.e. is pharmaceutically effective, can be determined by standard measures. Particularly, it can be determined by assessing cancer therapy efficacy. Cancer therapy efficacy, e.g., can be assessed by determining the time to disease progression, the increase of quality of life and/or by determining the response rate. Thus, the required dosage will depend on the severity of the condition being treated, the patient's individual response, the method of administration used, the cancer type, the tumor and the like. The skilled person is able to establish a correct dosage based on his general knowledge. Generally, the dose of the hydroxyalkylated starch component may also be administered independently from the state of the disease as the product is considered as non-toxic and dose limits are considered to be based on the current clinical experience (with e.g. Voluven® 10% labeled as solution of HES 130/0.4: 30 ml/kg/day and/or Volulyte® 6% labeled as solution of HES 130/0.4: 50 ml/kg/day). Recently the dosage recommendation was amended to Voluven® 10%: 18 ml/kg/day and/or Volulyte® 6%: 30 ml/kg/day.

The term "administering" as used herein, preferably, refers to the introduction of a compound (such as the hydroxyalkyl starch or a compound selected from the group consisting of cytostatica, biologicals with anti-cancer activity and hormones with anti-cancer activity) or of a pharmaceutical composition according to the invention, into subjects, such as, patients diagnosed with a hematological neoplasm. The term comprises administering by parenteral and enteral routes of administration. The parenteral routes of administration are selected from the group comprising intravascular, transmucosal, trans-/intradermal, intramuscular (i.m.), intravenous (i.v.), intradermal, subcutaneous (s.c.), intraperitoneal (i.p.), intraventricular, intracranial, vaginal, nasal, intratumoral, intraosseal, intrathecal and intrapulmonal. The enteral methods of administration are selected from the group comprising oral, nasal, sublingual and rectal, administration and administration by gavage (via feeding tube), such as a percutaneous endoscopic gastrostomy (PEG tube) or percutaneous jejunostomy feeding tube (PJG tube). It is to be understood that the route of administration may depend on the cancer to be treated.

According to the invention the preferred route of administration is the parenteral administration. It is further preferred that such parenteral route is an infusion, preferably into a blood vessel. The most preferred route of administration is an intravenous route.

Preferably, the administration of a single dose (bolus) of a therapeutically effective amount of the aforementioned compounds is over a period of 5 min to 5 h.

In the following the term "cytostatica" shall be understood to consist of one or more of the substances, which are known to be effective in chemotherapy, aiming at increased survival rates, extended life span of patients, reduction of malignant cell count, and/or the alleviation of symptoms in patients suffering from hematological neoplasms, by inhibiting cell growth. The term therefore comprises cytotoxic and cytostatic active ingredients.

It is understood that the group of substances named cytostatica is further characterized as being obtainable by chemical synthesis, as opposed to biotechnological synthesis. The term cytostatica shall not encompass HAS or HES, preferably also no other starch derivatives, most preferably no other polysaccharides.

The term "biologicals with anti-cancer activity" shall be understood to consist of proteins or nucleic acids produced by biotechnological methods with a cytotoxic and/or cytostatic effect on cancer cells. Examples are antibodies, such as cetuximab.

The term "hormones with anti-cancer activity" shall be understood to consist of biochemical compounds (including proteins) able to affect functions in remote cells or organs, whether produced and released by a cell, gland, organ or biosynthetically, and exerting an antiproliferative effect in cancer cells susceptible to the action of such hormones e.g. by expressing corresponding hormone receptors.

Hydroxyethylated starches for the treatment and prophylaxis of hypovolemia are in use, also as i.v. infusions, since many years and show no toxic side effects. The dose recommendations known from such other medical uses specify an upper limit due to physical limits only. Solutions labeled as "6% Hydroxyethyl Starch 130/0.4" in 0.9% sodium chloride can be administered repetitively over several days. Hence the patient can be provided with continued infusions of HES in combination with single doses or multiple doses of one or more compounds selected from the group consisting of cytostatica, biologicals with anti-cancer activity and hormones with anti-cancer activity to treat his cancer and inhibit the growth rate of the tumor.

The hydroxyalkylated starch may also be used in the so called watering therapy during or following a hematological neoplasm treatment regimen with e.g. cytostatics (Ko et al. (2011) Intravenous fluid therapy successfully prevents renal injury by gemcitabine in patients with pancreatic cancer. Pancreas 2011 July; 40(5): 784-6). Here an additional benefit of treating cancer hematological neoplasm, may be achieved besides the protection of organs e.g. kidneys and bladder, which is achieved by administering the watering solutions.

Preferably, the hydroxyalkyl starch is administered together with a suitable carrier, and/or a suitable diluent, such as preferably a sterile solution for i.v., i.m., i.p. or s.c. application.

It is further preferred that the route of administration involves a ready-to-use liquid solution of the HAS.

The term "subject", as used herein, relates to animals and, preferably, to mammals. In a preferred embodiment, the subject is a rodent such as a mouse or a rat. Even more preferred is the embodiment, wherein the subject is a primate. Most preferably, the subject is a human. According to the invention it is understood that the term "subject" also relates to an individual suffering from hematological neoplasm or an individual in need of treatment thereof. In a preferred embodiment of the invention the term "subject" describes a cancer patient, diagnosed with a hematological neoplasm.

The term "hydroxyalkyl starch" or "hydroxy alkylated starch" encompasses various hydroxyl-alkylated starches, as will be described in more detail below. These hydroxyalkyl starches may be further substituted.

Hydroxyalkyl starch is an ether derivative of partially hydrolyzed natural starches, in which hydroxyl groups in the starch are suitably hydroxyalkylated. Preferred hydroxyalkyl starches are hydroxypropyl starch and hydroxyethyl starch, with hydroxyethyl starch being especially preferred.

The current invention not only comprises a new medical use of hydroxyalkylated starches (HAS) that are substituted with an alkyl residue which carries a hydroxy function, but also those alkylated starches that are substituted with alternative alkyl groups. In one embodiment the alkyl groups carry thiol groups, also referred to as sulfhydryl group. In another embodiment those alkylated starches have the unsubstituted hydroxy functions (hydroxyl groups) in the glucose unit replaced by thio functions (thiol groups). In another embodiment, some of the glucose units of the alkylated starches are alkylated, wherein some of these alkylgroups carry thiol groups, and some carry hydroxyl functions, and wherein some of the C2, C3 and C6 positions may be substituted, preferably by thiol groups. These starches are referred to herein as thio-HAS. They have been described in more detail below and in PCT/EP2011/003458.

According to the current application an "alkyl group" is understood to comprise a linear or branched functional group or side-chain that consists of saturated hydrocarbons, preferably of a chain length of 2 to 12 carbon atoms. Said saturated hydrocarbon can be linear (general formula $-C_nH_{2n+1}$) wherein the carbon atoms are joined in a snake-like structure, such as propyl-, butyl-, pentyl-, hexyl-, heptyl-, octyl-, nonyl-, decanyl-, undecanyl- and dodecanyl-residues; or branched (general formula $-CnH2n+1$, wherein n is above or equal 3) wherein the carbon backbone splits off in one or more directions, comprising for example isopropyl-, isobutyl-, tert.-butyl, 1-isopentyl-, 2-isopentyl, 3-isopentyl-, neopentyl-rests.

Starch is a polysaccharide of the formula $(C_6H_{10}O_5)_n$ which is composed substantially of alpha-D-glucose units, coupled via glycoside linkages. Generally speaking, starch consists substantially of amylose and amylopectin. Amylose is composed of linear chains in which the glucose units are linked via alpha-1,4-glycosidic linkages. Amylopectin has a highly branched structure, with alpha-1,4-glycosidic linkages and alpha-1,6-glycosidic linkages.

Natural starches from which hydroxyalkyl starches may be prepared include cereal starches, grain legume starches and potato starches. Cereal starches include rice starches, wheat starches such as einkorn starches, spelt starches, soft wheat starches, emmer starches, durum wheat starches or kamut starches, maize starches, rye starches, oat starches, barley starches, triticale starches and millet starches such as sorghum starches or teff starches. Grain legume starches include bean starches, pea starches, lentil starches and lupine starches. Preferred natural starches from which hydroxyalkyl starches are prepared have a high content of amylopectin relative to amylose. The amylopectin content of these starches is, for example, at least 70% by weight, preferably at least 75% by weight, more preferably at least 80% by weight, more preferably at least 85% by weight, more preferably at least 90% by weight, such as up to 95% by weight, up to 96% by weight, up to 97% by weight, up to 98% by weight or up to 99% by weight or up to 100% by weight. Natural starches having an especially high amylopectin content are, for example, suitable potato starches such as waxy potato starches, which are preferably extracted from substantially amylose-free potatoes, which are either traditionally cultivated, e.g. the natural variety Eliane, or genetically modified amylopectin potato varieties, and starches from waxy varieties of cereals such as waxy maize or waxy rice.

Generally, hydroxyalkyl starch is prepared by breaking starch grains and cleaving the macromolecules to obtain molecules having a desired size. Cleaving can be carried out, for example, by enzymatic degradation, as for example using alpha-amylase and/or beta-amylase, and/or by means of acidic hydrolysis. Purification of the desired fractions can be accomplished, for example, by means of ultrafiltration, using membranes having a suitable cut-off limit, which allow the separation, for example, of low-molecular by-products having a molecular weight of up to 5000 Da or up to 1000 Da. Two or more cleaving stages can be carried out in series, with the possibility in each stage of using the same or different cleaving technologies. After each cleaving stage, the product obtained can be purified. The product ultimately obtained can be isolated, as for example by freeze-drying.

On the basis of the starch fractions thus obtained, hydroxyalkyl starch is prepared by etherification of hydroxyl groups. In general, all reactions known from the etherification of low-molecular alcohols may be contemplated, such as reactions without catalyst or with basic catalysts. The preferred methods in technical processes include the Michael addition of activated olefins, the Williams synthesis with nucleophilic substitution of compounds containing aliphatic halogen, or the reaction with oxiranes, also known as epoxides.

Concerning the preparation of hydroxyalkyl starch, more particularly of hydroxyethyl starch, reference is made, for example, to Sommermeyer et al., Chromatographia, 25, 1988, pp. 167-168; C. Jungheinrich et al., Clin. Pharmacokin., 44 (7), 2005, pp. 681-699; J.-M. Mishler IV, Pharmacology of hydroxyethyl starches, Oxford Medical Publications, 2002, pp. 1-30.

According to the present invention, the term "hydroxyalkyl starch" (HAS) refers to a starch derivative having a constitution according to the following formula (III)

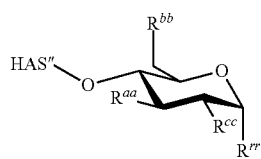
(III)

wherein the depicted ring structure is either a terminal or a non-terminal saccharide unit, which may be one anhydroglucose unit as described separately in this application, of the HAS molecule and wherein HAS" is a remainder, i.e. a residual portion of the hydroxyalkyl starch molecule, said residual portion forming, together with the depicted ring structure containing the residues $R^{aa}$, $R^{bb}$ and $R^{cc}$ and $R^{rr}$ the overall HAS molecule. In formula (III), $R^{aa}$, $R^{bb}$ and $R^{cc}$ are independently of each other hydroxyl, a linear or branched hydroxyalkyl group or —O-HAS".

Residue $R^{rr}$ is —O-HAS" in case the depicted ring structure is a non-terminal saccharide unit of the HAS molecule. In case the depicted ring structure is a terminal saccharide unit of the HAS molecule, $R^{rr}$ is —OH, and formula (III) shows this terminal saccharide unit in its hemiacetal form. This hemiacetal form, depending on e.g. the solvent, may be in equilibrium with the free aldehyde form as shown in the scheme below:

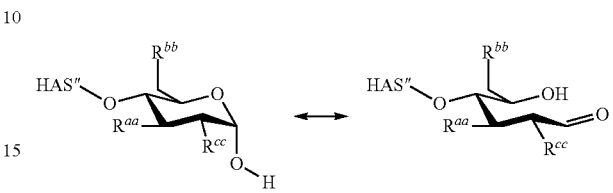

The term O-HAS" as used in the context of the residue $R^{rr}$ as described above is, in addition to the remainder HAS" shown at the left hand side of formula (III), a further remainder of the HAS molecule which is linked as residue $R^{rr}$ to the depicted ring structure of formula (III)

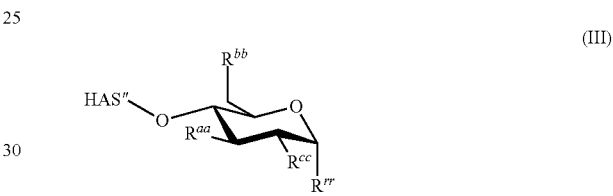
(III)

and forms, together with the residue HAS" shown at the left hand side of formula (III) and the depicted ring structure the overall HAS molecule.

Each remainder HAS" discussed above comprises, preferably essentially consists of—apart from terminal saccharide units—one or more repeating units according to formula (IIIa)

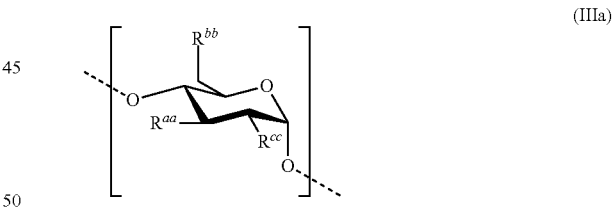
(IIIa)

According to the present invention, the HAS molecule shown in formula (III) is either linear or comprises at least one branching point, depending on whether at least one of the residues $R^{aa}$, $R^{bb}$, and $R^{cc}$ of a given saccharide unit comprises yet a further remainder —O-HAS". If none of the $R^{aa}$, $R^{bb}$ and $R^{cc}$ of a given saccharide unit comprises yet a further remainder —O-HAS", apart from the HAS" shown on the left hand side of formula (III), and optionally apart from HAS" contained in $R^{rr}$, the HAS molecule is linear.

Hydroxyalkyl starch comprising two or more different hydroxyalkyl groups is also conceivable. The at least one hydroxyalkyl group comprised in the hydroxyalkyl starch may contain one or more, in particular two or more, hydroxyl groups. According to a preferred embodiment, the at least one hydroxyalkyl group contains only one hydroxyl group.

According to the present invention, a hydroxyalkyl starch (HAS) according to the above-mentioned formula (III)

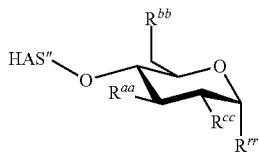
(III)

is disclosed for the treatment of hematological neoplasms. The saccharide units comprised in HAS", apart from terminal saccharide units, may be the same or different, and preferably have the structure according to the formula (IIIa)

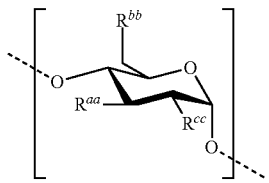
(IIIa)

as shown above. This unit is also described in more detail in the following:

A typical anhydroglucose unit of a hydroxyalkyl starch molecule has the following formula (I):

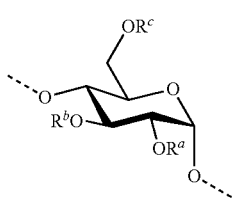
(I)

In formula (I), the residues $R^a$ (—$OR^a$ is depicted as $R^{cc}$ in formula III), $R^b$ (—$OR^b$ is depicted as $R^{aa}$ in formula III) and $R^c$ (—$OR^c$ is depicted as $R^{bb}$ in formula III) are independently [(—$CR^jR^k$)$_y$—O]$_z$—H, in which $R^j$ and $R^k$ are independently H or alkyl, preferably lower alkyl such as methyl or ethyl, preferably H;

y is an integer from 0 to 6, preferably from 2 to 4 such as 0, 1, 2, 3, 4, more preferably 2 or 3, more preferably 2;

z is an integer from 0 to 20, preferably from 0 to 10, more preferably from 0 to 6, more preferably from 0 to 4 such as 0, 1, 2, 3, 4, with the proviso that in case y is 0, z is likewise 0.

If there is a branching site of the macromolecule located on the glucose molecule, however, $R^c$ may also be a further chain of glucose molecules, such as, for example, (Glc-1, 4-Glc)$_n$-Glc, in which n may have a value from 0 to 20. The anhydroglucose units in such a side-chain may also be substituted, like the chain identified initially.

If the anhydroglucose unit is a unit of the hydroxyalkyl starch molecule which is not substituted by at least one hydroxyalkyl moiety, then the index z in $R^a$ and $R^b$ and $R^c$ is 0. If the anhydroglucose unit is a unit of the hydroxyalkyl starch molecule which is substituted by a hydroxyalkyl moiety in C2 position only, the index z is 0 in $R^b$ and $R^c$ and is greater than 0 in $R^a$. If the anhydroglucose unit is a unit of the hydroxyalkyl starch molecule which is substituted by a hydroxyalkyl moiety in C3 position only, the index z is 0 in $R^a$ and $R^c$ and is greater than 0 in $R^b$. If the anhydroglucose unit is a unit of the hydroxyalkyl starch molecule which is substituted by a hydroxyalkyl moiety in C6 position only, the index z is 0 in $R^a$ and $R^b$ and greater than 0 in $R^c$. If the anhydroglucose unit is a unit of the hydroxyalkyl starch molecule which is substituted by a hydroxyalkyl moiety in C2 and C3 position only, the index z is 0 in $R^c$ and is greater than 0 in $R^a$ and $R^b$. If the anhydroglucose unit is a unit of the hydroxyalkyl starch molecule which is substituted by a hydroxyalkyl moiety in C2 and C6 position only, the index z is 0 in $R^b$ and greater than 0 in $R^a$ and $R^c$. If the anhydroglucose unit is a unit of the hydroxyalkyl starch molecule which is substituted by a hydroxyalkyl moiety in C3 and C6 position only, the index z is 0 in $R^a$ and greater than 0 in $R^b$ and $R^c$. If the anhydroglucose unit is a unit of the hydroxyalkyl starch molecule which is substituted by a hydroxyalkyl moiety in C2 and C3 and C6 position, the index z is greater than 0 in $R^a$ and $R^b$ and $R^c$.

In one embodiment according to the invention the hydroxyalkyl starch is a pure hydroxypropyl starch, herein a respective residue $R^a$ or $R^b$ or $R^c$ with an index z greater than 0 has an index y of 3, and both $R^j$ and $R^k$ are H. Since multiple hydroxypropylation may occur during the preparation, the index z can be greater than 1, such as 2, 3 or more.

In addition, whenever the alkylation is carried out using epoxides a further form of the side-chain is formed. In this case, the hydroxy function is not located on the terminal C atom of the alkyl side-chain, but instead on $C^2$, i.e. the second C atom, counting from the ring. Following a propylation by means of the epoxide 1,2-epoxypropane, at least one of the residues $R^a$ or $R^b$ or $R^c$ would have the following appearance, for example: ($C^1R^jR^k$—$C^2R_j$(OH)—$C^3R^jR^k$H). After propylation by means of an unsubstituted 1,2-epoxypropane, in other words with methyloxirane ("propylene oxide"), $R^j$ and $R^k$ each are H.

In a preferred embodiment, the hydroxyalkyl starch is a pure hydroxyethyl starch, here a respective residue $R^a$ or $R^b$ or $R^c$ with index z greater than 0 has an index y which is 2, and both $R^j$ and $R^k$ are H. Since multiple hydroxyethylation may occur during the preparation, the index z can be greater than 1, such as 2, 3 or more. If, for example, a double hydroxyethylation takes place on a given hydroxyl group of an anhydroglucose unit, the index y and the index z are both 2, and the residues $R^j$ and $R^k$ are both H in one respective residue $R^a$ (or $R^b$ or $R^c$), which is, accordingly, —$CH_2$—$CH_2$—O—$CH_2$—$CH_2$—OH.

It is also possible that different alkylating agents are used (mixed alkylation), which means that $R^a$, $R^b$ and $R^c$ are alternatively to be represented in such a way that y may have different values—accordingly, for example, in the case of mixed hydroxyethylation and hydroxypropylation, y may be 2 in one residue and 3 in the other residue. Furthermore, in a residue R with z>0, there may be a side-chain in which the value y may have different values, e.g. 2 or 3.

Mixed alkylation with epoxides may also result in the possible presence of structural units of the form [(—$CR^jR^k$)$_y$—O]$_z$—H and of the form [—$C^1R^jR^k$—$C^2R^j$($C^3R^jR^k$H)—O]$_z$—H in one or various residues $R^a$, $R^b$ or $R^c$ in different numbers.

Furthermore, the glucose polymer may also be substituted by a thioalkyl residue. In principle, therefore, it is also possible for the above-described embodiments to exist with a sulphur atom instead of an oxygen atom in the substituted side chain. In this case, at least one of the residues $R^a$, $R^b$ and $R^c$ may be —[(—$CR^jR^k$)$_y$—S]$_z$—H or [—$C^1R^jR^k$—$C^2R^j$($C^3R^jR^kH$)—S]$_z$—H. According to the invention, thiohydroxyalkyl starches of this kind are likewise disclosed for the treatment of hematological neoplasms.

Processes for preparing thiohydroxyalkyl starches can be found in the PCT Application "Conjugates comprising Hydroxyalkyl Starch and a Cytotoxic Agent and Process for their Preparation" published in January 2012, WO2012/004005 (PCT/EP2011/003458); in particular, reference is made to the preparation processes on pages 245-252 (beginning with "1.3. Special Procedures" up to and including "1.4.9. General procedure for the synthesis of SH-HES using sodium sulfide as nucleophile") and, where necessary for comprehension, to the associated tables 6 to 9 on pages 259-263.

In a preferred embodiment the hydroxyalkyl starch according to the invention is hydroxyethyl starch, hydroxypropyl starch or hydroxybutyl starch, with hydroxyethyl starch being particularly preferred.

According to the present invention, the hydroxyalkyl starch (HAS) is preferably a hydroxyethyl starch (HES), the hydroxyethyl starch preferably having a structure according to the following formula (III)

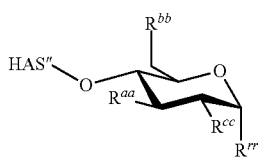
(III)

wherein $R^{aa}$, $R^{bb}$ and $R^{cc}$ are independently of each other selected from the group consisting of —O-HES", and —[O—$CH_2$—$CH_2$]$_s$—OH, wherein s is in the range of from 0 to 4 and wherein HAS", is the remainder of the hydroxyethyl starch and is abbreviated with HES". Residue $R^{rr}$ is either —O-HES" or, in case the formula (III) shows the terminal saccharide unit of HES, $R^{rr}$ is —OH.

As a polymer, and owing to the preparation processes, hydroxyalkyl starch is a polydisperse compound in which the individual hydroxyalkyl starch molecules may differ with respect to the degree of polymerization, the number and the pattern of the branching sites, and the substitution pattern, i.e. the number and/or sites of the hydroxyalkyl groups. Therefore, hydroxyalkyl starch is usually characterized by statistically averaged parameters. These are, generally, the average molecular weight and parameters which characterize the substitution pattern. The latter parameters are typically identified as degree of substitution (DS), molecular substitution (MS) and C2/C6 ratio, i.e. the ratio of the number of anhydroglucose units substituted in C2 position to the number of anhydroglucose units substituted in C6 position, or the ratio of Mw relative to Mn (Mw/Mn), which is usually referred to as PDI (polydispersity index) and characterizes the spread of the molecular weight distribution.

Hydroxyalkyl starch may be substituted with hydroxyalkyl groups not only at the C2 and C6 sites, but also at the C3 site, but this information is usually omitted when referring to a specific type of HAS.

The second parameter specifying a HAS usually refers to the degree of molecular substitution MS and the third parameter either refers to the ratio of substitutions at C2 versus substitutions at C6 (C2/C6 ratio) or to the PDI.

Generally speaking, there are two ways of statistically describing the average molecular weight of hydroxyalkyl starch. The first parameter is the number-average molecular weight, commonly referred to as Mn or $M_n$; the second parameter is the weight-average molecular weight, commonly referred to as Mw or $M_w$.

The molecular weight can be determined, for example, by means of gel permeation chromatography with multiple-angle light-scattering detection (GPC/MALLS/RI). Reference is made, for example, to W.-M. Kulicke et al., Starch, 45 (12), 1993, pp. 445-450. Alternatively, the molecular weight can be determined using flow-FFF/MALLS, as for example in accordance with European Pharmacopoeia 7.0, 01/2011:1785, p. 984 or else by B. Wittgren et al., Int. J. Polym. Anal. Charact. 7 (1-2), 2002, pp. 19-40.

In this context the number average molecular weight is defined by equation 1:

$$\overline{M}_n = \frac{\sum_i n_i \cdot M_i}{\sum_i n_i} \quad (1)$$

in which $n_i$ is the number of hydroxyalkyl starch molecules of species i having molar mass $M_i$. $\overline{M}_n$ indicates that this is an average value, but the line is typically omitted.

The weight average molecular weight $M_w$ is defined by the following equation:

$$\overline{M}_w = \frac{\sum_i n_i \cdot M_i^2}{\sum_i n_i M_i} \quad (2)$$

in which $n_i$ is the number of hydroxyalkyl starch molecules of species i having molar mass $M_i$. $\overline{M}_w$ indicates that this is an average value, but the line is typically omitted.

In the context of the present description the term "mean molecular weight" refers to the weight determined by the MALLS (multiple angle laser light scattering)-GPC method.

Hydroxyalkyl starches according to the invention have a mean molecular weight (Mw or MW) varying from as low as about 20 kDa to mean molecular weights up to 1300 kDA.

The ratio of Mw relative to the Mn (Mw/Mn), which is usually referred to as PDI, polydispersity index, is a parameter characterizing the spread of the molecular weight distribution. The closer this parameter is to the value 1, the less dispers the molecular weight distribution is.

According to the invention typical PDI values are in the range of from 4.0 to 1.1.

The substitution pattern can be determined quantitatively, at least partially, using $^1$H NMR or by a more elaborate method, by means of high-resolution $^{13}$C NMR. Reference is made to Y. M. Liu et al., Chin. Chem. Lett. 13 (11), 2002, pp. 1097-1099, and to W.-M. Kulicke et al., Starch, 45 (12), 1993, pp. 445-450. In general there are three customary parameters which describe the degree of substitution of hydroxyalkyl starch.

The first parameter, which is identified as "DS" (degree of substitution), describes the ratio of the number of substituted anhydroglucose units to the total number of all the anhydroglucose units. In view of this definition, the theoretical maximum value of DS is 1.0.

The parameter DS can be determined, for example, in accordance with W. Banks et al., Br. J. Pharmac., 47, 1973, pp. 172-178, O. Larm et al., Starch, 33 (7), 1981, pp. 240-244, or Sommermeyer et al., Starch, 44 (6), 1992, pp. 215-218.

The second parameter, which is typically identified as "MS" (molecular substitution), describes the ratio of the number of hydroxyalkyl residues (in mol) which have been added by hydroxyalkylation to the glucose molecules of the starch macromolecule, relative to the number of glucose monomers in the molecule.

Assuming that the alkylation results in the addition of a single alkyl unit per hydroxy function, the degree of molar substitution indicates what proportion of the three hydroxy units the glucose units on the starch molecule have been substituted or replaced by hydroxyalkyl units. Herein a substitution degree of 1 equals a 100% of substitution of one of the three free hydroxy groups. Hence theoretically the range of substitution could vary from 0.1 to 3, wherein three indicated that all three hydroxy units would be 100% substituted. There is a number of different types of HAS in the market, and their substitution degrees vary from 0.3 to 2.

The parameter MS may be determined in accordance with Ying-Che Lee et al., Anal. Chem. 55, 1983, pp. 334-338; or K. L. Hodges et al., Anal. Chem. 51, 1979, p. 2171. According to these methods, a known amount of the hydroxyalkyl starch is subjected to an ether cleavage in xylene, with addition of adipic acid and hydriodic acid. The amount of iodoalkane released is subsequently determined by means of gas chromatography, using toluene as an internal standard and iodoalkane calibration solutions as external standards.

The third parameter, which is identified as the C2/C6 ratio, describes the ratio of the number of anhydroglucose units substituted in C2 position to the number of anhydroglucose units substituted in C6 position. During the preparation of the hydroxyalkyl starch, the C2/C6 ratio can be influenced via the amount of base used for the hydroxyalkylation reaction. Generally speaking, the higher the concentration of base, the greater the number of hydroxyl groups which are hydroxyalkylated in C6 position.

The parameter C2/C6 can be determined, for example, in accordance with Sommermeyer et al., Krankenhauspharmazie 8 (8), 1987, pp. 271-278, especially page 273.

Various types of hydroxyalkyl- and hydroxyethyl starch, therefore, are usually described by a statement of their average molecular weight, expressed in kDa, their degree of molar substitution (MS), and their degree of branching (C2/C6), or by an indication of their polydispersity (Mw/Mn).

The present invention provides a fundamentally new active therapeutic agent for the treatment of hematological neoplasms, which reduces the problematic side effects associated with the administration of cancer therapeutics. In particular, the toxic side effects associated with the administration of one or more compounds selected from the group consisting of cytostatica, biologicals with anti-cancer activity and hormones with anti-cancer activity, can be reduced when the hematological neoplasms are treated with a reduced dosing thereof.

The present invention therefore relates to a method of treatment wherein HAS is administered for the treatment of hematological neoplasms either as the only medicament or as a first medicament, which may either be administered before or after the administration of second medicament, which is characterized as being a therapeutically active compound selected from the group consisting of cytostatica, biologicals with anti-cancer activity and hormones with anti-cancer.

It was unexpectedly found that the administration of HAS to mammals that were inoculated subcutaneously with cancer cells from a hematological neoplasms, and were therefore forming a tumor, alleviated their symptoms and resulted in a significant growth reduction of the tumor, whilst not adversely affecting their health or body weight.

Advantageously, the hydroxyalkyl starch or the pharmaceutical composition comprising said hydroxyalkyl starch is not toxic and triggers hardly any side effects when given intravenously, which is of great advantage when compared to a cytotoxic agent. Hence wherein the max. dosage of a conventional cytotoxic agent is limited severely by its toxic side effects, a patient can receive repeated doses or continuous infusion of hydroxyethyl starches on a daily basis—potentially in addition to a standard-of-care treatment with one or more compounds selected from the group consisting of cytostatica, biologicals with anti-cancer activity and hormones with anti-cancer activity.

Preferably the method of treatment as described allows the reduction of the dose of the second compound as compared to clinical practice with the compound alone (as in a in a standard of care treatment) whilst preserving the therapeutic efficacy.

It is preferred that the hydroxyalkyl starch that is administered to a subject has a mean molecular weight MW of above 20 kDa, preferably above 40 kDa, and even more preferably a MW greater than 65 kDa. Preferably the MW is also not higher than 1300 kDa. More preferably the MW is in the range of from 75 to 1200 kDa, and more preferably in the range of from 90 to 800 kDa.

In one embodiment, the hydroxyalkyl starch (HAS) according to the invention has a molar substitution degree MS of the HAS in the range of from 0.1 to 1.5. Preferred embodiments comprise particular ranges of molar substitutions values of 0.15 to 1.5, 0.2 to 1.5, 0.3 to 1.5, 0.4 to 1.5, 0.5 to 1.5, 0.6 to 1.5, 0.7 to 1.5, 0.75 to 1.5, more preferably in the range of 0.1 to 1.3, 0.1 to 1.0, 0.1 to 0.8, 0.1 to 0.6, and 0.1 to 0.5 and also preferably in the range of from 0.90 to 1.4, such as 0.90, 0.95, 1.0, 1.05, 1.1, 1.15, 1.2, 1.25, 1.3, 1.35 or 1.4. A particularly preferred range is from 0.1 to 1.0, more preferably from 0.1 to 0.6, more preferably from 0.25 to 0.55.

According to an especially preferred embodiment, the hydroxyalkyl starch derivative has a mean molecular weight MW in the range of from 80 to 1200 kDa and a MS in the range of from 0.1 to 1.5. Preferred embodiments comprise particular ranges of molar substitutions values of 0.15 to 1.45, 0.3 to 1.45, 0.45 to 1.45, 0.6 to 1.45, 0.7 to 1.45, 0.75 to 1.45, more preferably in the range of 0.1 to 0.5 and preferably in the range of from 0.90 to 1.4, such as 0.90, 0.95, 1.0, 1.05, 1.1, 1.15, 1.2, 1.25, 1.3, 1.35 or 1.4, more preferably a molar substitution MS in the range of from 0.1 to 1.30, or 0.1 to 0.5.

In an especially preferred embodiment, the hydroxyalkyl starch derivative has a mean molecular weight MW in the range of from 30 to 700 kDa and a molar substitution in the range of from 0.1 to 0.7; more preferably a mean molecular weight MW in the range of from 80 to 700 kDa and a MS in the range of from 0.1 to 0.7.

In one embodiment the C2/C6 ratio of HAS, is in the range of from 0.5 to 20, more preferably in the range of from 2 to 20, 18, 2 to 17, 2 to 14, 2 to 12, 2 to 10, 2 to 8, 2 to 6, 2 to 5, or 2 to 4. In another preferred embodiment said C2/C6 substitution is in the range of from 4 to 12, 6 to 12, 7 to 12, or preferably in the range of from 7 to 10, more preferably in the range from 8 to 9. In another preferred embodiment said C2/C6 substitution is in the range of from 4 to 6, more preferably is 5.7.

In a preferred embodiment, the polydispersion index PDI is in the range of from 1.1 to 4.0, more preferably in the range of from 1.1 to 3.5, 1.1 to 3, 1.1 to 2.5, 1.1 to 2, 1.1 to 1.5, 1.1 to 1.4, 1.1 to 1.3 and 1.1 to 1.2. In another preferred embodiment the PDI is in the range of from 1.2 to 4, 1.35 to 4, 1.5 to 4, 1.7 to 4, 1.8 to 4, 1.9 to 4, 2 to 4, 2.5 to 4 or 2 to 4, or 1.4 to 3.0.

All of these ranges are considered to comprise values that differ from the precise numbers given by about a tenth of their numeric value.

Preferably, the hydroxyalkyl starch according to the invention, in particular the hydroxyethyl starch, as described above, has a mean molecular weight MW (weight mean) above the renal threshold.

In another preferred embodiment the hydroxyalkyl starch according to the invention, in particular the hydroxyethyl starch, as described above, has a mean molecular weight MW (weight mean) below the renal threshold.

The renal threshold is determined according to the method described by Waitzinger et al. (Clin. Drug Invest. 1998; 16: 151-160) and reviewed by Jungheinrich et al. (Clin. Pharmacokinet. 2006; 44(7): 681-699). Preferably, the renal threshold is denoted to mean a molecular weight MW equal to or higher than 40 kDa, or 45 kDa or 60 kDa or 65 kDa.

In the following, hydroxyalkyl starch structures are described in more detail, which comprise several different preferred embodiments of the described class of HAS, which is used in a combination therapy with one or more compounds selected from the group consisting of cytostatica, biologicals with anti-cancer activity and hormones with anti-cancer activity.

In one preferred embodiment the hydroxyalkylated starch is a hydroxyethylated starch known under the name "HES 130/0.4". Despite the name "HES 130/0.4" this is a hydroxyethylstarch with a mean molecular weight of 105 kDa, according to the standard measurement and calibration method described in European Pharmacopoeia 7.0, 01/2011:1785, p. 984, with a molar substitution degree of 0.38-0.45, a mean molar substitution degree of 0.42. Its C2/C6 ratio is between 8.0 and 12.0. Its PDI is about 2, i.e. between 1.7 and 2.3. It is commercially available, for example as a 10% solution in 0.9% NaCl solution, under the registered trade name Voluven®. The difference between the value of the MW 130 of the publicly known specification of "HES 130/0.4" and the amended specification to HES 105/0.4 results from a change in the method calibration used for determining the Mw of HAS. Whereas previously the determination was performed according to Sommermeyer et al. (Krankenhauspharmazie, 8, 1987, 08, p. 271-278), the amended value (Mw 105) has been determined according to the calibration as described in European Pharmacopoeia 7.0, 01/2011:1785, p. 984. The difference in the method is the value of the light scattering value dn/dc, wherein in the Sommermeyer method a dn/dc value of 0.135 is used, this value changed to 0.147+/-0.001 in the "Pharmacopoeia method".

In another preferred embodiment according to the invention HAS is a hydroxyethylated starch known as "HES 100/1.0/1.3". This is a hydroxyethylstarch with a mean molecular weight of 100 kDa, determined according to Sommermeyer et al.; and with a mean molecular weight of about 84 kDa (75-93 kDa), determined according to European Pharmacopoeia 7.0, 01/2011:1785, p. 984; and a molar substitution degree of 1.0±0.05. Its C2/C6 ratio is 5.0-6.0 or preferably 5.7 and the PDI is 1.3±0.1.

Often the name indicated in parentheses such as "HES 200/0.5" refers to the old measurement, but it is explained herein, which Mw values will be generated if measured according to European Pharmacopeia (as cited before). The Mw values in the application (which are not part of the name) refer to those determined according to European Pharmacopoeia 7.0, 01/2011:1785, p. 984 with the calibration method defined therein using a dn/dc value of 0.147-0.149, unless specifically mentioned otherwise.

Another embodiment is a hydroxyethylated starch known as "HES 70/0.4/1.8" for the treatment of a hematological neoplasm. This is a hydroxyethylstarch with a mean molecular weight of 70 kDa, a molar substitution degree of 0.4 and a PDI of 1.8.

Another embodiment is a hydroxyethylated starch known as "HES 70/0.5" for the treatment of a hematological neoplasm. This is a hydroxyethylstarch with a mean molecular weight of 70 kDa, a molar substitution degree of 0.5.

Another embodiment is a hydroxyethylated starch HES 100/0.1/2.0 for the treatment of a hematological neoplasm. This is a hydroxyethylstarch with a mean molecular weight of 100 kDa, a molar substitution degree of 0.1 and a PDI of 2.0.

Another embodiment is a hydroxyethylated starch named as "HES 100/0.1/2.0" for the treatment of a hematological neoplasm. This is a hydroxyethylstarch with a mean molecular weight of 130 kDa, a molar substitution degree of 0.1 and a PDI of 2.0.

Another embodiment is a hydroxyethylated starch known as "HES 100/0.7/1.3" for the treatment of a hematological neoplasm. This is a hydroxyethylstarch with a mean molecular weight of 100 kDa, a molar substitution degree of 0.7 and a PDI of 1.3.

Another embodiment is a hydroxyethylated starch known as "HES 100/1.0/1.1" for the treatment of a hematological neoplasm. This is a hydroxyethylstarch with a mean molecular weight of 100 kDa, a molar substitution degree of 1.0 and a PDI of 1.1.

Another embodiment is a hydroxyethylated starch known as "HES 150/0.7/1.3" for the treatment of a hematological neoplasm. This is a hydroxyethylstarch with a mean molecular weight of 150 kDa, a molar substitution degree of 0.7 and a PDI of 1.3.

Another embodiment is a hydroxyethylated starch known as "HES 150/1.0/1.3" for the treatment of a hematological neoplasm. This is a hydroxyethylstarch with a mean molecular weight of 150 kDa, a molar substitution degree of 1.0 and a PDI of 1.3.

Another embodiment is a hydroxyethylated starch known as "Viastarch" with a mean molecular weight of: Mw 150-300 kDa, a molar substitution degree of MS 0.40-0.50, further characterized by Mw of lowest 10% fraction >=25 kDa, Mw of highest 10% fraction <=2000 kDa, which may also be referred to as "HES 180/0.45", for the treatment of a hematological neoplasm.

Another embodiment is a hydroxyethylated starch known as "HES 200/0.5" for the treatment of a hematological neoplasm. This is a hydroxyethylstarch with a mean molecular weight of 200 kDa, further characterized by a Mw 170-290, and of a molar substitution degree of 0.43 to 0.55. This HES may be further characterized by Mw of lowest 10% fraction >15 kDa, and Mw of highest 10% fraction <600 kDa.

Another embodiment is a hydroxyethylated starch known as "Pentastarch" with a mean molecular weight of: Mw 200-300 kDa, and a MS of 0.40-0.50; further characterized by Mw of lowest 10% fraction >=15 kDa, Mw of highest 10% fraction <=1500 kDa, which can be referred to as "HES 250/0.45", for the treatment of a hematological neoplasm.

Another embodiment is a hydroxyethylated starch known as "HES 300/1.0/1.3" for the treatment of a hematological neoplasm. This is a hydroxyethylstarch with a mean molecular weight of 250+/−17 kDa (or 300 kDa according to Sommermeyer et al.), a molar substitution degree of 1.0+/−0.05 and a PDI of 1.3+/−0.1.

Another embodiment is a hydroxyethylated starch with a mean molecular weight of 300 kDa, a substitution degree Ds of below 0.4 as described in WO 00/48637, for the treatment of a hematological neoplasm.

Another embodiment is a hydroxyethylated starch known as "HES 450/0.7" for the treatment of a hematological neoplasm. This is a hydroxyethylstarch with a mean molecular weight of 450 kDa (Mw 400-500 kDa), which may be further specified by a Mw of lowest 10% fraction >=25 kDa, and a Mw of highest 10% fraction <=3000 kDa; and a molar substitution degree of 0.7 (MS 0.65-0.75).

Another embodiment is a hydroxyethylated starch with a mean molecular weight of 500 kDa according to the method referred to under Sommermeyer et al. and a molar substitution degree of 0.28 and a C2/C6 ratio of 8.7 described in and according to U.S. Pat. No. 5,502,043 "Use of hydroxyethyl starch for improvement of microcirculation" to Weidler et al., in example 3, for the treatment of a hematological neoplasm.

Another embodiment is a hydroxyethylated starch with a mean molecular weight of 500 kDa and a molar substitution degree MS between 0.25 and 0.5 and a C2/C6 ratio of 2 to below 8 described in and according to European patent EP1732953B (claim 1), for the treatment of a hematological neoplasm.

Another embodiment is a hydroxyethylated starch with a mean molecular weight of 600 kDa and a molar substitution degree of 0.5 described in and according to European patent EP0402724B by Fresenius AG for the treatment of a hematological neoplasm.

Another embodiment is a hydroxyethylated starch known as "HES 700/0.5/2.5" for the treatment of a hematological neoplasm. This is a hydroxyethylstarch with a mean molecular weight of 600+/−40 kDa (or 700 kDa according to Sommermeyer et al.), a molar substitution degree of 0.5+/−0.05 and a PDI of 2.5.

Another embodiment is a hydroxyethylated starch known as "Hetastarch", with a mean molecular weight of: Mw 550-800 kDa, MS 0.70-0.80, Mw of lowest 10% fraction >=13 kDa, Mw of highest 10% fraction <=4000 kDa; which can be described as "HES 700/0.7" for the treatment of a hematological neoplasm.

Another embodiment is a hydroxyethylated starch known as "HES 700/0.7/2.0" for the treatment of a hematological neoplasm. This is a hydroxyethylstarch with a mean molecular weight of 600+/−40 kDa (or 700 kDa according to Sommermeyer et al.), a molar substitution degree of 0.7+/−0.05 and a PDI of 2.0.

Another embodiment is a hydroxyethylated starch known as "HES 700/1.0/1.5" for the treatment of a hematological neoplasm. This is a hydroxyethylstarch with a mean molecular weight of 600+/−40 kDa (or 700 kDa according to Sommermeyer et al.), a molar substitution degree of 1.0+/−0.05 and a PDI of 1.5.

Another embodiment is a hydroxyethylated starch known as "HES 700/1.3/1.5" for the treatment of a hematological neoplasm. This is a hydroxyethylstarch with a mean molecular weight of 600+/−40 kDa (or 700 kDa according to Sommermeyer et al.), a molar substitution degree of 1.3+/−0.05 and a PDI of 1.6+/−0.1.

Another embodiment is a hydroxyethylated starch known as "HES 60/1.3/1.3" for the treatment of a hematological neoplasm. This is a hydroxyethylstarch with a mean molecular weight of 50+/−5 kDa (or 60 kDa according to Sommermeyer et al.), a molar substitution degree of 1.3+/−0.05 and a PDI of 1.3+/−0.1.

Another embodiment is a hydroxyethylated starch of a mean molecular weight Mw of 1000 kDa and a substitution degree Ds between 4 and 10 for, as described in U.S. Pat. No. 6,680,305 for the treatment of a hematological neoplasm.

Another embodiment is a hydroxyethylated starch known as "HES 70000", also referred to as "HES 70/0.55" with a mean molecular weight Mw of 60-80 kDa for the treatment of a hematological neoplasm. Preferably it has a MS of 0.55-0.61. Preferably it has a PDI of 2.3+/−0.1. Another embodiment is a hydroxyethylated starch known of a mean molecular weight Mw of 70 kDa and a C2/C6 ratio between 2 to 8 as described in and according to A. N. Belder and B. Norman in Carbohydrate Research, Vol 10, 1969, p. 391-394 for the treatment of a hematological neoplasm.

It is understood that while different compounds for treatment are described as embodiments these compounds are also disclosed for use in such a treatment. Further, the method for treating a hematological neoplasm which comprises administration of such a compound as described herein in a therapeutically effective amount to the subject in need thereof is also disclosed.

In a preferred embodiment the therapeutic activity of HAS results in an inhibitory effect on the proliferating activity of the cancer cells, wherein HAS reduces the proliferation rate of hematological neoplasm cells. This is based on the observations which were made when the tumor tissue of HES-treated and untreated mice was compared.

In an embodiment of the invention HAS is therapeutically active in reducing or inhibiting the proliferation rate or arresting the mitotic cycle of cancer cells or cells proliferating without physiological control, wherein the cancer is a hematological neoplasm.

In another embodiment of the invention HAS is therapeutically active in reducing the cancer cell proliferation rate by arresting cancer cells in the mitotic cycle, wherein the cancer is a hematological neoplasm.

It could be shown that HAS solutions have a direct effect on the growth rate of tumors caused by subcutaneous application of leukemic cancer cells, whereas it can be assumed that the treatment with HAS solutions does not affect normally proliferating cells in healthy tissues.

In a preferred embodiment according to the invention the cancer is selected from the group of cancer derived from the blood, the bone marrow and the lymphatic system, preferably from the group of hematological neoplasms. Preferably the group consists of all of those hematopoietic and lymphoid cancers as listed in table 1.

It is preferred that the hematologic neoplasm is selected from the group consisting of leukemia and lymphoma.

TABLE 1

(from Swerdlow SH, Campo E, Harris NL et al. "WHO classification of tumours of haematopoietic and lymphoid tissues" World Health Organization classification of tumors 2 (4th ed.). International Agency for Research on Cancer)

MYELOPROLIFERATIVE NEOPLASMS

Chronic myelogenous leukemia, BCR-ABL1-positive
Chronic neutrophilic leukemia
Polycythemia vera
Primary myelofibrosis
Essential thrombocythemia
Chronic eosinophilic leukemia, not otherwise specified
Mastocytosis
Myeloproliferative neoplasms, unclassifiable

MYELOID AND LYMPHOID NEOPLASMS ASSOCIATED WITH EOSINOPHILIA AND ABNORMALITIES OF PDGFRA, PDGFRB, OR FGFR1

Myeloid and lymphoid neoplasms associated with PDGFRA rearrangement
Myeloid neoplasms associated with PDGFRB rearrangement
Myeloid and lymphoid neoplasms associated with FGFR1 abnormalities

MYELODISPLASTIC/MYELOPROLIFERATIVE NEOPLASMS (MDS/MPN)

Chronic myelomonocytic leukemia
Atypical chronic myeloid leukemia, BCR-ABL1-negative
Juvenile myelomonocytic leukemia
Myelodysplastic/myeloproliferative neoplasm, unclassifiable
Provisional entity: refractory anemia with ring sideroblasts and thrombocytosis

MYELODISPLASTIC SYNDROMES

Refractory cytopenia with unilineage dysplasia
Refractory anemia
Refractory neutropenia
Refractory thrombocytopenia
Refractory anemia with ring sideroblasts
Refractory cytopenia with multilineage dysplasia
Refractory anemia with excess blasts
Myelodysplastic syndrome with isolated del(5q)
Myelodysplastic syndrome, unclassifiable
Childhood myelodysplastic syndrome
Provisional entity: refractory cytopenia of childhood

ACUTE MYELOID LEUKEMIA (AML) AND RELATED PRECURSOR NEOPLASMS

Acute myeloid leukemia with recurrent genetic abnormalities
AML with t(8;21)(q22;q22); RUNX1-RUNX1T1
AML with inv(16)(p13.1q22) or t(16;16)(p13.1;q22); CBFB-MYH11
APL with t(15;17)(q22;q12); PML-RARA
AML with t(9;11)(p22;q23); MLLT3-MLL
AML with t(6;9)(p23;q34); DEK-NUP214
AML with inv(3)(q21q26.2) or t(3;3)(q21;q26.2); RPN1-EVI1
AML (megakaryoblastic) with t(1;22)(p13;q13); RBM15-MKL1
Provisional entity: AML with mutated NPM1
Provisional entity: AML with mutated CEBPA
Acute myeloid leukemia with myelodysplasia-related changes
Therapy-related myeloid neoplasms
Acute myeloid leukemia, NOS (=not otherwise specified)
AML with minimal differentiation
AML without maturation
AML with maturation
Acute myelomonocytic leukemia
Acute monoblastic/monocytic leukemia
Acute erythroid leukemia
Pure erythroid leukemia
Erythroleukemia, erythroid/myeloid
Acute megakaryoblastic leukemia
Acute basophilic leukemia
Acute panmyelosis with myelofibrosis
Myeloid sarcoma
Myeloid proliferations related to Down syndrome
Transient abnormal myelopoiesis
Myeloid leukemia associated with Down syndrome
Blastic plasmacytoid dendritic cell neoplasm

ACUTE LEUKEMIA OF AMBIGUOUS LINEAGE

Acute undifferentiated leukemia
Mixed phenotype acute leukemia with t(9;22)(q34;q11.2); BCR-ABL1
Mixed phenotype acute leukemia with t(v;11q23); MLL rearranged
Mixed phenotype acute leukemia, B-myeloid, NOS
Mixed phenotype acute leukemia, T-myeloid, NOS
Provisional entity: natural killer (NK) cell lymphoblastic leukemia/lymphoma TABLE 1-continued (from Swerdlow SH, Campo E, Harris NL et al. "WHO classification of tumours of haematopoietic and lymphoid tissues" World Health Organization classification of tumors 2 (4th ed.). International Agency for Research on Cancer)

PRECURSOR LYMPHOID NEOPLASMS

B lymphoblastic leukemia/lymphoma
B lymphoblastic leukemia/lymphoma, NOS
B lymphoblastic leukemia/lymphoma with recurrent genetic abnormalities
B lymphoblastic leukemia/lymphoma with t(9;22)(q34;q11.2);BCR-ABL 1
B lymphoblastic leukemia/lymphoma with t(v;11q23);MLL rearranged
B lymphoblastic leukemia/lymphoma with t(12;21)(p13;q22) TEL-AML1 (ETV6-RUNX1)
B lymphoblastic leukemia/lymphoma with hyperdiploidy
B lymphoblastic leukemia/lymphoma with hypodiploidy
B lymphoblastic leukemia/lymphoma with t(5;14)(q31;q32) IL3-IGH
B lymphoblastic leukemia/lymphoma with t(1;19)(q23;p13.3);TCF3-PBX1
T lymphoblastic leukemia/lymphoma

MATURE B-CELL NEOPLASMS

Chronic lymphocytic leukemia/small lymphocytic lymphoma
B-cell prolymphocytic leukemia
Splenic marginal zone lymphoma
Hairy cell leukemia
Splenic lymphoma/leukemia, unclassifiable
Splenic diffuse red pulp small B-cell lymphoma
Hairy cell leukemia variant
Lymphoplasmacytic lymphoma
Waldenström macroglobulinemia
Heavy chain diseases
α Heavy chain disease
γ Heavy chain disease
μ Heavy chain disease
Plasma cell myeloma
Solitary plasmacytoma of bone
Extraosseous plasmacytoma
Extranodal marginal zone lymphoma of mucosa-associated lymphoid tissue (MALT lymphoma)
Nodal marginal zone lymphoma
Pediatric nodal marginal zone lymphoma
Follicular lymphoma
Pediatric follicular lymphoma
Primary cutaneous follicle centre lymphoma
Mantle cell lymphoma
Diffuse large B-cell lymphoma (DLBCL), NOS
T-cell/histiocyte rich large B-cell lymphoma
Primary cutaneous DLBCL, leg type
EBV-positive DLBCL of the elderly
DLBCL associated with chronic inflammation
Lymphomatoid granulomatosis
Primary mediastinal (thymic) large B-cell lymphoma
Intravascular large B-cell lymphoma
ALK-positive large B-cell lymphoma
Plasmablastic lymphoma
Large B-cell lymphoma arising in HHV8-associated multicentric Castleman disease
Primary effusion lymphoma
Burkitt lymphoma
B-cell lymphoma, unclassifiable, with features intermediate between diffuse large B-cell lymphoma and Burkitt lymphoma
B-cell lymphoma, unclassifiable, with features intermediate between diffuse large B-cell lymphoma and classical Hodgkin lymphoma

MATURE T-CELL AND NK-CELL NEOPLASMS

T-cell prolymphocytic leukemia
T-cell large granular lymphocytic leukemia
Chronic lymphoproliferative disorder of NK cells
Aggressive NK-cell leukemia
Systemic EBV-positive T-cell lymphoproliferative disease of childhood
Hydroa vacciniforme-like lymphoma
Adult T-cell leukemia/lymphoma
Extranodal NK/T-cell lymphoma, nasal type
Enteropathy-associated T-cell lymphoma
Hepatosplenic T-cell lymphoma
Subcutaneous panniculitis-like T-cell lymphoma
Mycosis fungoides
Sézary syndrome
Primary cutaneous CD30+ T-cell lymphoproliferative disorders
Lymphomatoid papulosis
Primary cutaneous anaplastic large cell lymphoma
Primary cutaneous γδ T-cell lymphoma

TABLE 1-continued (from Swerdlow SH, Campo E, Harris NL et al. "WHO classification of tumours of haematopoietic and lymphoid tissues" World Health Organization classification of tumors 2 (4th ed.). International Agency for Research on Cancer)

Primary cutaneous CD8+ aggressive epidermotropic cytotoxic T-cell lymphoma
Primary cutaneous CD4+ small/medium T-cell lymphoma
Peripheral T-cell lymphoma, NOS
Angioimmunoblastic T-cell lymphoma
Anaplastic large cell lymphoma, ALK-positive
Anaplastic large cell lymphoma, ALK-negative
HODGKIN LYMPHOMA Nodular lymphocyte predominant Hodgkin lymphoma
Classical Hodgkin lymphoma
Nodular sclerosis classical Hodgkin lymphoma
Lymphocyte-rich classical Hodgkin lymphoma
Mixed cellularity classical Hodgkin lymphoma
Lymphocyte-depleted classical Hodgkin lymphoma
HISTIOCYTIC AND DENDRITIC CELL NEOPLASMS Histiocytic sarcoma
Langerhans cell histiocytosis
Langerhans cell sarcoma
Interdigitating dendritic cell sarcoma
Follicular dendritic cell sarcoma
Fibroblastic reticular cell tumor
Intermediate dendritic cell tumor
Disseminated juvenile xanthogranuloma
POSTTRANSPLANTATION LYMPHOPROLIFERATIVE DISORDERSs (PTLDs)

Early lesions
Plasmacytic hyperplasia
Infectious mononucleosis-like PTLD
Polymorphic PTLD
Monomorphic PTLD (B- and T/NK-cell types)
Classical Hodgkin lymphoma type PTLD It is preferred that the hematologic neoplasm of the lymphatic system is selected from the group of lymphoma. It is further preferred that the group of lymphoma does not comprise primary CNS lymphoma of the brain and/or spinal cord. It is further preferred that the group of lymphoma does not comprise primary CNS lymphoma.

The group of lymphoma preferably consists of lymphomas of the type of mature B cell neoplasms and mature T-cell and NK-cell neoplasms and histiocytic and dendritic cell neoplasms; as well as Hodgkin lymphomas. Some lymphomas are known by different names, for example, some lymphomas of the type of B mature cell neoplasm, may also be referred to as Non-Hodgkin lymphoma. The Multiple myeloma, for example, which is also known as Morbus Kahler, or as plasma cell myeloma is a Non-Hodgkin lymphoma, but also a mature B cell neoplasm.

It is especially preferred that the hematological neoplasm is selected from the group consisting of lymphomas of mature B cell neoplasms.

It is especially preferred that the hematological neoplasm is selected from the group consisting of Small lymphocytic lymphoma, Splenic marginal zone lymphoma, Splenic lymphoma, Lymphoplasmacytic lymphoma, Extranodal marginal zone lymphoma of mucosa-associated lymphoid tissue, Nodal marginal zone lymphoma, Follicular lymphoma, Primary cutaneous follicle centre lymphoma, Mantle cell lymphoma, Heavy chain diseases, Solitary plasmacytoma of bone, Extraosseous plasmacytoma, Diffuse large B-cell lymphoma, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma, Burkitt lymphoma, B-cell lymphoma—unclassifiable, with features intermediate between diffuse large B-cell lymphoma and Burkitt lymphoma and B-cell lymphoma—unclassifiable, with features intermediate between diffuse large B-cell lymphoma and classical Hodgkin lymphoma.

It is especially preferred that the hematological neoplasm is selected from the group consisting of lymphomas of mature T-cell and K-cell neoplasms.

It is especially preferred that the hematological neoplasm is selected from the group consisting of Systemic EBV-positive T-cell lymphoproliferative disease of childhood, Hydroa vacciniforme-like lymphoma, Adult T-cell lymphoma, Extranodal NK/T-cell lymphoma, nasal type Enteropathy-associated T-cell lymphoma, Hepatosplenic T-cell lymphoma, Subcutaneous panniculitis-like T-cell lymphoma, Mycosis fungoides, Sézary syndrome, Primary cutaneous CD30+ T-cell lymphoproliferative disorders, Primary cutaneous anaplastic large cell lymphoma, Primary cutaneous γδ T-cell lymphoma, Primary cutaneous CD8+ aggressive epidermotropic cytotoxic T-cell lymphoma, Primary cutaneous CD4+ small/medium T-cell lymphoma, Peripheral T-cell lymphoma, NOS; Angioimmunoblastic T-cell lymphoma, Anaplastic large cell lymphoma—ALK-positive and Anaplastic large cell lymphoma—ALK-negative.

In another preferred embodiment the lymphoma is Hodgkin lymphoma. Preferably the Hodgkin lymphoma is selected from the group consisting of Nodular lymphocyte predominant Hodgkin lymphoma, Classical Hodgkin lymphoma, Nodular sclerosis classical Hodgkin lymphoma, Lymphocyte-rich classical Hodgkin lymphoma, Mixed cellularity classical Hodgkin lymphoma and Lymphocyte-depleted classical Hodgkin lymphoma.

In preferred embodiment the hematological neoplasm is a Histiocytic and dendritic cell neoplasms. Preferably it is selected from the group consisting of Histiocytic sarcoma, Langerhans cell histiocytosis, Langerhans cell sarcoma, Interdigitating dendritic cell sarcoma, Follicular dendritic cell sarcoma, Fibroblastic reticular cell tumor, Intermediate dendritic cell tumor and Disseminated juvenile xanthogranuloma.

It is another preferred embodiment wherein the hematological neoplasm is a posttransplantation lymphoproliferative disorder (PTLD) according to table 1.

Preferably the hematological neoplasm is a Non-Hodgkin lymphoma.

In a preferred embodiment the hematological neoplasms, preferably those of the lymphoid system, are at a stage wherein they have not yet formed tumors. It is preferred that the lymphomas are treated before they form tumors.

It is further preferred that the hematological neoplasms are selected from the group of hematological neoplasms which do not form tumors.

It is preferred that the hematological neoplasm is selected from the group of leukemia. It is preferred that the group of leukemia does not include blastic leukemia.

Clinically and pathologically, leukemia is subdivided into a variety of large groups. The first division is between its acute and chronic forms. Additionally, the diseases are subdivided according to which kind of blood cell is affected. This split divides leukemia into lymphoblastic or lymphocytic leukemia and myeloid or myelogenous leukemia.

In lymphoblastic or lymphocytic leukemia, the cancerous change takes place in a type of marrow cell that normally goes on to form lymphocytes, which are infection-fighting immune system cells. Most lymphocytic leukemia involve a specific subtype of lymphocyte, the B cell. In myeloid or myelogenous leukemia, the cancerous change takes place in a type of marrow cell that normally goes on to form white blood cells, some other types of white cells, and platelets.

Preferably the hematological neoplasms comprise the group of myeloproliferative neoplasms, myeloid and lymphoid neoplasms with eosinophilia and abnormalities of PDGFRA, PDGFRB or FGFR1, myelodysplastic/myeloproliferative, myelodysplastic syndromes, acute myeloid leukemia (AML) and related precursor neoplasms, acute leukemia of ambiguous lineage and precursor lymphoid neoplasms, all according to table 1.

Preferably the hematological neoplasm is selected from the group of acute myelogenous leukemia, acute lymphoblastic leukemia, chronic myelogenous leukemia and chronic lymphoblastic leukemia. Preferably the hematological neoplasm is an acute leukemia, more preferably an Acute myeloid leukemia (AML), also known as acute myelogenous leukemia or acute nonlymphocytic leukemia (ANLL), which is a cancer of the myeloid line of blood cells, characterized by the rapid growth of abnormal white blood cells that accumulate in the bone marrow and interfere with the production of normal blood cells. According to the WHO Acute myeloid leukemia with recurrent genetic abnormalities includes AML with translocations between chromosome 8 and 21, AML with inversions in chromosome 16, APL with translocations between chromosome 15 and 17, AML with translocations in chromosomes 9 and 11. AML with multi-lineage dysplasia includes patients who have had a prior myelodysplastic syndrome (MDS) or myeloproliferative disease (MPD) that transforms into AML. This category of AML occurs most often in elderly patients and often has a worse prognosis. AML and MDS, therapy-related includes patients who have had prior chemotherapy and/or radiation and subsequently develop AML or MDS. These leukemia may be characterized by specific chromosomal abnormalities, and often carry a worse prognosis. AML not otherwise categorized includes subtypes of AML that do not fall into the above categories.

Preferably the group of leukemia also comprises, or most preferably consists of acute leukemia of ambiguous lineage (also known as mixed phenotype or biphenotypic acute leukemia), which occur when the leukemic cells cannot be classified as either myeloid or lymphoid cells, or where both types of cells are present.

Preferably the group of leukemia is also comprising, or most preferably consisting of leukemia of the type of mature B-cell neoplasms. Preferably the hematological neoplasm is therefore selected from the group consisting of lymphatic leukemia, chronic lymphocytic leukemia B-cell prolymphocytic leukemia, hairy cell leukemia, splenic leukemia, T-cell prolymphocytic leukemia, T-cell large granular lymphocytic leukemia, aggressive NK-cell leukemia and adult T-cell leukemia. Preferably the group of leukemia also comprises the chronic lymphoproliferative disorder of NK cells.

It is also preferred that the hematological neoplasm is selected from the group consisting of leukemia of the type of mature T-cell and K-cell neoplasms. Preferably the group of leukemia also comprises, or most preferably consists of T-cell prolymphocytic leukemia, T-cell large granular lymphocytic leukemia, Chronic lymphoproliferative disorder of NK cells and Aggressive NK-cell leukemia.

Another preferred embodiment of the present invention pertains to the use of the hydroxyalkyl starch, or the pharmaceutical composition, according to the present invention for the manufacture of a medicament for the treatment of hematological neoplasms, wherein the hydroxyalkyl starch is the therapeutically active ingredient, which is administered to a subject, preferably prior to or after the administration of a pharmaceutical composition containing one or more compounds selected from the group consisting of cytostatica, biologicals with anti-cancer activity and hormones with anti-cancer activity, wherein the hydroxalkyl starch may be administered within the same treatment day, within the same hour or with a treatment break in between, of up to several days or weeks.

Treatment methods according to the invention may be targeted to all hematological neoplasms, preferably to all leukemia cancer types mentioned herein, and the HAS administered may comprise all types of HAS, and preferably HES disclosed herein.

The following especially preferred embodiments are also comprised in the invention:

1. A hydroxyalkyl starch (HAS), as therapeutically active compound, for use in the treatment of a subject suffering from a hematological neoplasm.
2. A hydroxyalkyl starch (HAS), for use according to embodiment 1, wherein a therapeutically effective amount is administered to said subject.
3. A hydroxyalkyl starch according to embodiment 1 or 2, wherein the hematological neoplasm is selected from the group of leukemia and lymphoma.
4. A hydroxyalkyl starch according to any of the preceding embodiments, wherein the hematological neoplasm is selected from the group of leukemia and lymphoma and wherein this group does not comprise primary CNS lymphoma.
5. A hydroxyalkyl starch (HAS) for use according to embodiments 1 to 4, wherein the treatment comprises administration of HAS, or of a pharmaceutical composition comprising HAS, and wherein the administration results in at least one of reduced tumor growth rates, reduced cancer cell growth rates, reduced proliferative activity, reduced number of cancer cells or the prevention of metastases.

6. A hydroxyalkyl starch (HAS) for use according to embodiments 1 to 4, wherein the treatment comprises at least one of reducing tumor growth rate, reducing the number of highly proliferating cells, the number of cancer cells, reducing the frequency of cancer cell division, reducing cancer cell growth rates and preventing the formation of a tumor.

7. A hydroxyalkyl starch (HAS) for use according to any of the preceding embodiments, wherein the treatment comprises inhibiting cancer cell infiltration into peripheral organs and preventing the spread of cancer cells.

8. A hydroxyalkyl starch (HAS) for use according to any of the preceding embodiments, wherein the treatment comprises inhibiting hematological neoplasm cells from proliferating.

9. A hydroxyalkyl starch (HAS) for use according to any of the preceding embodiments, wherein the treatment comprises inhibiting hematological neoplasm cells from proliferating, whilst not affecting normally growing cells.

10. A hydroxyalkyl starch (HAS) for use according to any of the preceding embodiments, wherein the HAS is administered prior to or after the administration of one or more second compounds.

11. A hydroxyalkyl starch (HAS) for use according to any of the preceding embodiments, wherein a dose reduction of one or more second compounds is achieved, compared to the dose given in a treatment without administration of HAS.

12. A hydroxyalkyl starch (HAS) for use according to embodiments 10 and 11, wherein the one or more second compounds are selected from the group consisting of cytostatica, biologicals with anti-cancer activity and hormones with anti-cancer activity.

13. A hydroxyalkyl starch (HAS) for use according to the embodiments 10 and 11, wherein the one or more second compounds are selected from the group consisting of cytostatica and biologicals with anti-cancer activity.

14. A hydroxyalkyl starch (HAS) for use according to the embodiments 10 and 11, wherein the one or more second compounds are selected from the group consisting of cytostatica.

15. A hydroxyalkyl starch (HAS) for use according to embodiments 10 to 14, wherein the group of cytostatica comprises or preferably consists of alkylating agents, alkyl sulfonates, antimetabolites, anti-tumor antibiotics, topoisomerase inhibitors, small molecule tyrosine kinase inhibitors, mitotic inhibitors differentiating agents, proteasom inhibitors and plerixafor.

16. A hydroxyalkyl starch (HAS) for use according to embodiment 10 to 13, wherein the group of biologicals with anti-cancer activity comprises or preferably consists of antibody tyrosine kinase inhibitors, monoclonal antibodies and immunomodulating proteins.

17. A hydroxyalkyl starch (HAS) for use according to any of the preceding embodiments, wherein the hydroxyalkyl starch comprises at least one structural unit according to the following formula (I)

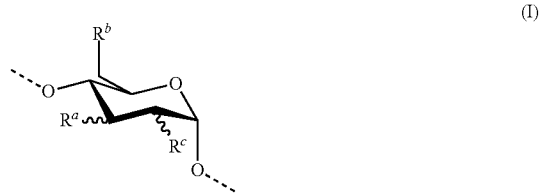

wherein $R^a$, $R^b$ and $R^c$ are independently of each other selected from the group consisting of —O-HAS", —[O—($CR^wR^x$)—($CR^yR^z$)]$_x$—OH, —[O—($CR^wR^x$)—($CR^yR^z$)]$_y$—XH, wherein $R^w$, $R^x$, $R^y$ and $R^z$ are independently of each other selected from the group consisting of hydrogen and alkyl, y is an integer in the range of from 0 to 20, preferably in the range of from 0 to 4, and x is an integer in the range of from 0 to 20, preferably in the range of from 0 to 4, and wherein at least one of $R^a$, $R^b$ and $R^c$ is [O—($CR^wR^x$)—($CR^yR^z$)]$_y$—XH and wherein X is selected from the group consisting of —S—, and —O—.

18. A hydroxyalkyl starch (HAS) for use according to any of the preceding embodiments, wherein the hydroxyalkyl starch has a mean molecular weight Mw between 20 and 1300 kDa.

19. A hydroxyalkyl starch (HAS) for use according to any of the preceding embodiments, wherein the hydroxyalkyl starch has a mean molecular weight Mw between 40 and 1300 kDa.

20. A hydroxyalkyl starch (HAS) for use according to any of the preceding embodiments, wherein the hydroxyalkyl starch has a mean molecular weight Mw between 65 and 1300 kDa.

21. A hydroxyalkyl starch (HAS) for use according to any of the preceding embodiments, wherein the hydroxyalkyl starch has a mean molecular weight Mw between 70 and 1200 kDa.

22. A hydroxyalkyl starch (HAS) for use according to any of the preceding embodiments, wherein the hydroxyalkyl starch has a mean molecular weight Mw between 75 and 800 kDa.

23. A hydroxyalkyl starch (HAS) for use according to any of the preceding embodiments, wherein the hydroxyalkyl starch has a mean molecular weight Mw between 90 and 800 kDa.

24. A hydroxyalkyl starch (HAS) for use according to any of the preceding embodiments, wherein the hydroxyalkyl starch has a mean molecular weight Mw between 100 and 700 kDa.

25. A hydroxyalkyl starch (HAS) for use according to any of the preceding embodiments, wherein the hydroxyalkyl starch has a mean molecular weight Mw between 100 and 110 kDa.

26. A hydroxyalkyl starch (HAS) for use according to any of the preceding embodiments, wherein the hydroxyalkyl starch has a mean molecular weight Mw above the renal threshold.

27. A hydroxyalkyl starch (HAS) for use according to embodiment 1 to 19, wherein the hydroxyalkyl starch has a mean molecular weight Mw below the renal threshold.

28. A hydroxyalkyl starch (HAS) for use according to any of the preceding embodiments, wherein the hydroxyalkyl starch has a molecular substitution MS between 0.1 and 1.5.

29. A hydroxyalkyl starch (HAS) for use according to any of the preceding embodiments, wherein the hydroxyalkyl starch has a molecular substitution MS between 0.1 and 1.3.
30. A hydroxyalkyl starch (HAS) for use according to any of the preceding embodiments, wherein the hydroxyalkyl starch has a molecular substitution MS between 0.1 and 1.1.
31. A hydroxyalkyl starch (HAS) for use according to any of the preceding embodiments, wherein the hydroxyalkyl starch has a molecular substitution MS between 0.1 and 0.9.
32. A hydroxyalkyl starch (HAS) for use according to any of the preceding embodiments, wherein the hydroxyalkyl starch has a molecular substitution MS between 0.3 and 0.8.
33. A hydroxyalkyl starch (HAS) for use according to any of the preceding embodiments, wherein the hydroxyalkyl starch has a molecular substitution MS between 0.3 and 0.7.
34. A hydroxyalkyl starch (HAS) for use according to embodiment 21 wherein the hydroxyalkyl starch has a mean molecular weight between 80 and 230 kDa and a molecular substitution MS between 0.3 and 0.6.
35. A hydroxyalkyl starch (HAS) for use according to embodiment 33 wherein the hydroxyalkyl starch has a mean molecular weight of 100 to 110 kDa and a molecular substitution MS between 0.3 and 0.5.
36. A hydroxyalkyl starch (HAS) for use according to embodiment 21 wherein the hydroxyalkyl starch has a mean molecular weight between 150 and 200 kDa and a molecular substitution MS between 0.4 and 0.5.
37. A hydroxyalkyl starch (HAS) for use according to embodiment 33 wherein the hydroxyalkyl starch has a mean molecular weight of 105 kDa and a molecular substitution MS of 0.42.
38. A hydroxyalkyl starch (HAS) for use according to embodiment 23 wherein the hydroxyalkyl starch has a mean molecular weight between 400 and 700 kDa and a molecular substitution MS between 0.6 and 0.8.
39. A hydroxyalkyl starch (HAS) for use according to any of the preceding embodiments wherein the hydroxyalkyl starch is hydroxyethyl starch.
40. A pharmaceutical composition comprising hydroxyalkyl starch (HAS) for use in the treatment of hematological neoplasms according to any of the preceding embodiments, wherein the HAS is the sole ingredient with a therapeutic activity in treating cancer.
41. A method of treating a subject suffering from a hematological neoplasm comprising administering a therapeutically effective amount of a hydroxyalkyl starch according to any of the preceding embodiments, before or after administering one or more second compounds selected from the group consisting of cytostatica, biologicals with anti-cancer activity and hormones with anti-cancer activity thereby inhibiting progression of cancer, preferably by reducing the proliferation rate of the cancer cells, preferably whilst not reducing the proliferation rate of normal cells.
42. A method of treating a subject suffering from a hematological neoplasm wherein the treating comprises administering to a subject diagnosed with a hematological neoplasm a therapeutically effective amount of HAS according to any of the preceding embodiments, wherein the treating comprises reducing the proliferation rate of the hematological neoplastic cells, and wherein no second therapeutically active compound has been administered to said subject.
44. A method of treating a subject suffering from a hematological neoplasm according to embodiments 41 and 42, wherein the reducing of the proliferation rate comprises arresting the cancer cells in the mitotic cycle.

DESCRIPTION OF THE FIGURES

In FIG. 3 the inhibitory effect of the hydroxyalkyl starch HES 130/0.4 on JURKAT cells (ALL cells) is shown.

In FIG. 4 the inhibitory effect of hydroxyalkyl starch HES 130/0.4 on TF-1 cells (AML cells) is shown.

In FIG. 5 the inhibitory effect of the hydroxyalkyl starch HES 130/0.4 on MEG-01 cells (CML cells) is shown.

In FIG. 6 the inhibitory effect of the hydroxyalkyl starch HES 130/0.4 on K562 cells (CML cells) is shown.

EXAMPLES

Example 1

Figure 1:
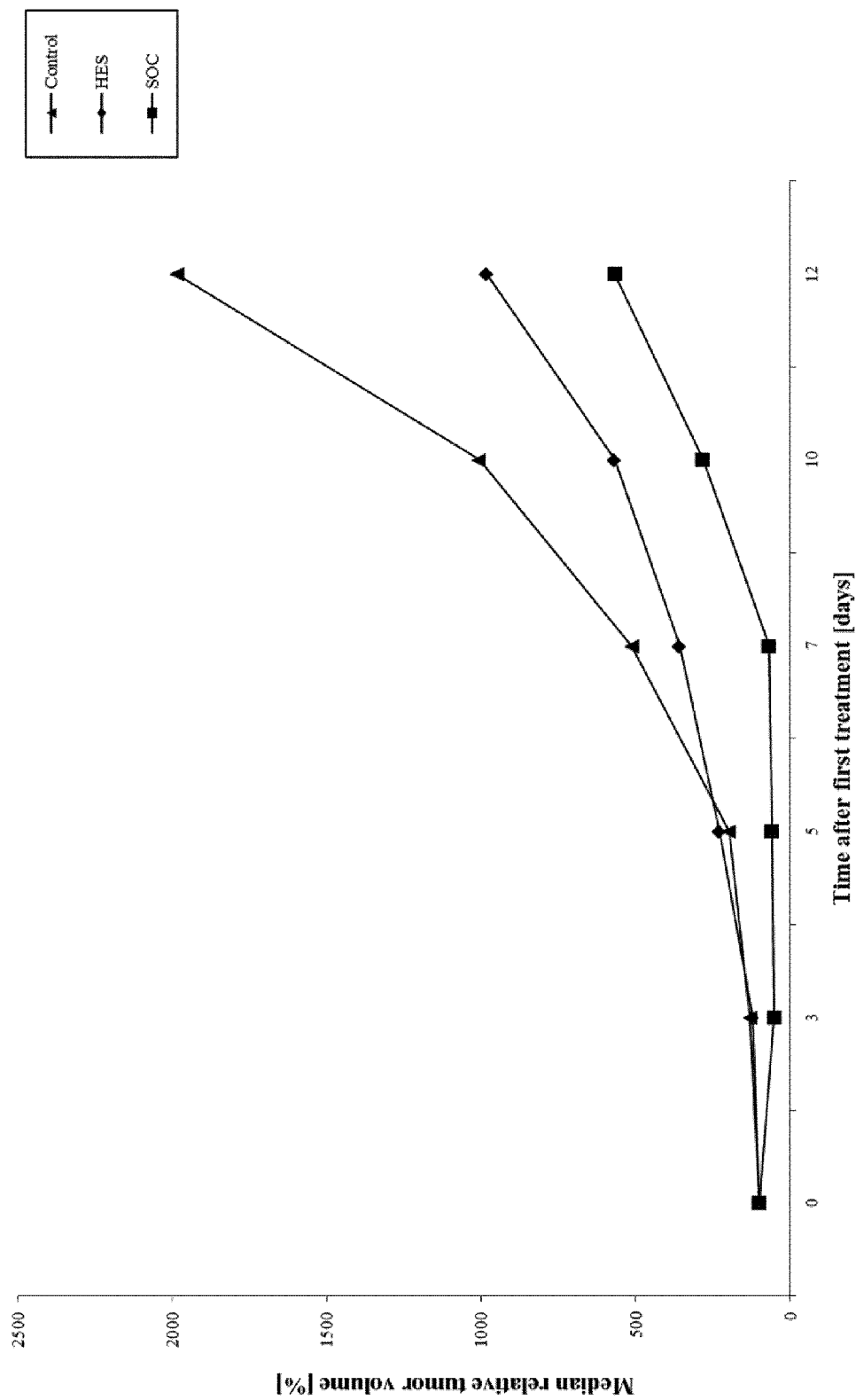
FIG. 1 shows the development of the relative tumor volume of mice inoculated with EOL-1 tumor cells over time as observed in example 1. Values on the Y-axis indicate the median relative tumor volume in percent, values on the X-axis indicate the time in days after the start of treatment. The substances are indicated by the following symbols: the "▲" (black up-pointing triangle) is used when 0.9% isotonic saline (NaCl) was administered to mice intravenously twice weekly, indicated as "Control". The "■" (big black square) is used when cyclophosphamide (75 mg/kg, single dose on day 0) was administered to mice intraperitoneally, indicated as "SOC". The "♦" (black diamond) is used when Voluven® 10% was administered to mice intravenously twice weekly, indicated as "HES".
Figure 2:
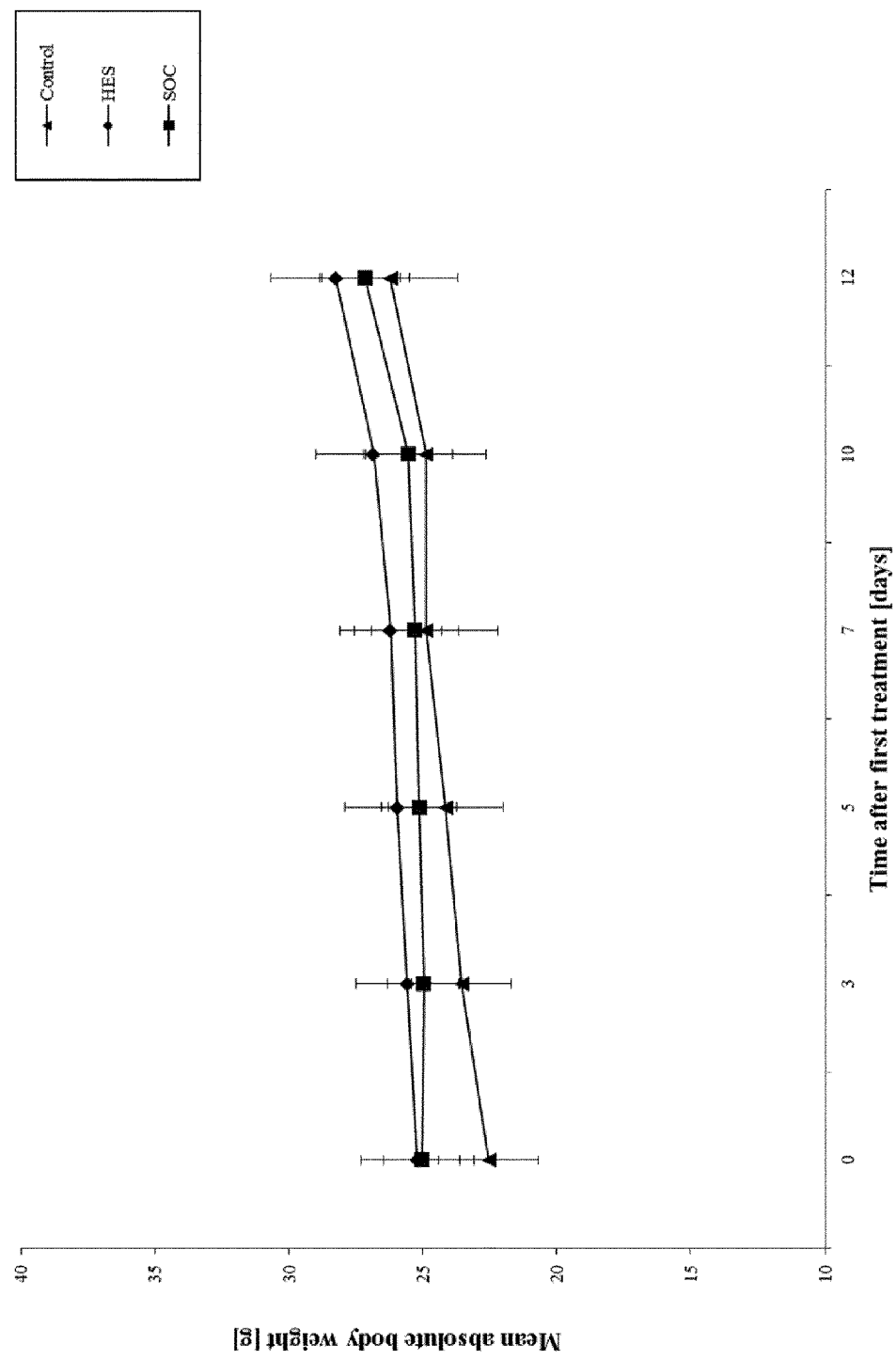
FIG. 2 shows the development of the body weight of mice inoculated with EOL-1 tumor cells over time as observed in example 1. Values on the Y-axis indicate the mean body weight in gram±the standard deviation (sd). Values on the X-axis indicate the time in days after the start of treatment. The substances are indicated by the following symbols: the "▲" (black up-pointing triangle) is used when 0.9% isotonic saline (NaCl) was administered to mice intravenously twice weekly, indicated as "Control". The "■" (big black square) is used when cyclophosphamide (75 mg/kg, single dose on day 0) was administered to mice intraperitoneally, indicated as "SOC". The "♦" (black diamond) is used when Voluven® 10% was administered to mice intravenously twice weekly, indicated as "HES".

In this example the HES type commercially available under the name Voluven® 10%, labelled as 2000 mg/kg "HES 130/04" as described in detail above was used.

Summary: Adult male NOD/SCID mice bearing tumors from the EOL-1 myelogenous leukemic cell line were either treated with a single i.p. injection of cyclophosphamide (Endoxan®) at a dose of 75 mg/kg or with the plasma volume expander Voluven® 10% i.v. into the tail vein (20 ml/kg) to determine tumor growth and body weight over the course of the experiment.

Substances: Cyclophosphamide (available under the name Endoxan®) was obtained from Baxter Oncology GmbH (Lot 2D714D; Halle, Germany) and was stored at 2-8° C. until use. Voluven® 10% (labelled as "hydroxyethyl starch 130/0.4" in 0.9% sodium chloride for injection) was obtained as a ready-to-use product from Fresenius Kabi Austria GmbH (Lot 14FC3308; Linz, Austria) and was stored at room temperature until use.

The final solution of cyclophosphamide was prepared immediately before injection by dissolving an appropriate amount of the substance in saline 0.9% (Lot 12495407, B. Braun Vet Care GmbH, Tuttlingen, Germany) to a final dose of 7.5 mg/ml.

All solutions were prepared and injected under sterile conditions.

TABLE 2

Preparation of injection solutions

| Substance | Dose | Application volume/ mouse (20 g) | Stock | Saline (ml) | Volume total (ml) |
| --- | --- | --- | --- | --- | --- |
| Saline | 20 ml/kg | 400 µl | Original solution | — | 10 |
| Voluven ® 10% | 20 ml/kg | 400 µl | Original solution | — | 10 |
| Cyclophosphamid | 75 mg/kg | 200 µl | 500 mg | 66.7 | 66.7 |

Animals: Adult male NOD/SCID mice (TACONIC Europe, Lille Skensved, Denmark) were used in the study. At the start of the experiment they were 6-8 weeks of age and had a median body weight between 20 and 25 g.

All mice were maintained under strictly controlled and standardized barrier conditions. They were housed—maximum five mice/cage—in individually ventilated cages (Macrolon Typ-II, system Techniplast, Italy) under following environmental conditions: 22+/−1° C. room temperature, 50+/−10% relative humidity, 12 hour-light-dark-rhythm. They received autoclaved food and bedding (Ssniff, Soest, Germany) and acidified (pH 4.0) drinking water ad libitum.

Animals were stratified to the experimental groups with 5 mice each after tumors had reached a palpable tumor size. At treatment initiation the ears of the animals were marked and each cage labelled with the cage number, study number, and animal number per cage.

Tumor Model

The human acute myelogeneous leukemia EOL-1 cell line was used as s.c. xenotransplantation model in immunodeficient male NOD/SCID mice. The human myelogeneous leukemia cell line EOL-1 (ACC386) was obtained from Leibniz Institute DSMZ-Deutsche Sammlung von Mikroorganismen and Zellkulturen GmbH, Braunschweig. Cells were grown in RPMI 1640, supplemented with 1% L-glutamine, and 10% foetal calf serum (FCS), in T150 cell culture flasks at 37° C., 90% humidity and 5% $CO_2$. EOL-1 cells are obtained from a human eosinophilic leukemia cell line, show cytological features of myeloblasts under normal culture conditions, and differentiate not only phenotypically but also functionally into eosinophils upon a number of stimuli. EOL-1 cells are particularly useful for analyzing leukemic cell differentiation and the properties of malignant eosinophils.

On study day −10 $1\times10^7$ tumor cells in 100 µl PBS were transplanted s.c. into the left flank of each mouse. After 10 days the tumors were palpable with a mean size of 0.1 $cm^3$ and the mice were stratified into 3 groups with 5 mice per group based on individual tumor volume to obtain groups with a comparable mean tumor volume and a minimum standard deviation. On the same day treatment was initiated according to table 3 below. In this model cyclophosphamide is the reference drug (SOC):

TABLE 3

| Group | Treatment | Dose | Route of application | Regimen |
| --- | --- | --- | --- | --- |
| A | Saline | 20 ml/kg | i.v. | Twice per week |
| B | Voluven ® 10% | 20 ml/kg | i.v. | Twice per week |
| C | Cyclophosphamide | 75 mg/kg | i.p. | Single dose (day 0) |

Individual tumor volume (TV) was calculated from two perpendicular diameters obtained by measurements using a calliper-like instrument three times a week.

TV was calculated according to the following formula: TV $[cm^3]=(width^2\times length)/2$. For calculation of the relative tumor volume (RTV) the tumor volumes at each measurement day were related to the day of first treatment. At each measurement day the median and mean tumor volumes per group and also the treated to control (T/C) values in percent were calculated. Individual body weights of mice were determined thrice weekly and body weight changes serve as toxicity parameter. The mean body weight per group and the body weight change (BWC) in relation to the start of treatment were calculated.

Mice were sacrificed when the tumor reached a diameter of more than 1.5 cm in one direction. At necropsy, all animals were weighed and killed by cervical dislocation.

Statistical Evaluation

Tumor volume was analyzed using descriptive data analysis and was graphically displayed as median value.

Results

All tumors in the control group (group A) showed progressive growth. The single i.p. treatment of EOL-1 myelogeneous leukemic-bearing mice with 75 mg/kg of cyclophosphamide induced a significant inhibition of tumor growth. Administration of Voluven® 10% i.v. twice weekly showed a moderate inhibitory activity and thereby demonstrated an inhibitory potential of alkylated starches in the growth of leukemic cells (see FIG. 1).

Treatment with Voluven® 10% had no effect on body weight development and thus no obvious treatment related toxicity.

Example 2

The objective of this study was to investigate potential effects of hydroxyethyl starch ("HES 130/0.4") on cell viability of different leukemia cell lines. The 50% inhibition concentration (IC50) was determined in 28 different leukemia cell lines using the commercially available "Prestoblue fluorescence cell viability assay" after incubation with different "HES 130/0.4" concentrations for screening reasons. The concentration range of the tested HES was 100 mg/ml-391 ng/ml.

PrestoBlue® reagent is a resazurin-based solution that functions as a cell viability indicator by using the reducing power of living cells to quantitatively measure the proliferation of cells. The PrestoBlue® reagent contains a cell-permeant compound that is blue in color and virtually non-fluorescent. When added to cells, the PrestoBlue® reagent is modified by the reducing environment of the viable cell and turns red in color and becomes highly fluorescent. This change can be detected using fluorescence or absorbance measurements (see e.g. Int J Microbiol. 2013; 2013: 420601; published online Apr. 4, 2013 doi: 10.1155/2013/420601 PMCID PMC3638707).

Each cell line was treated with the test item, either HES or the standard chemotherapy drug cisplatin at different concentrations. Cisplatin served as positive reference. The incubation time of cells with both substances was 72 h.

TABLE 4

Cell Lines tested and culture medium used

| No. | Cancer Type | Cell Line | Source | Culture Medium |
|---|---|---|---|---|
| 1 | ALL | CCRF-SB | ATCC | RPMI1640 + 10% FBS |
| 2 | ALL | Jurkat | ATCC | RPMI1640 + 10% FBS |
| 3 | ALL | MHH-CALL-2 | DSMZ | RPMI1640 + 10% FBS |
| 4 | ALL | Molt-4 | SIBS | RPMI1640 + 10% FBS |
| 5 | ALL | MUTZ-5 | DSMZ | RPMI1640 + 10% FBS |
| 6 | ALL | NALM 6 | SIBS | IMDM + 10% FBS |
| 7 | ALL | PEER IE6 | SIBS | IMDM + 10% FBS |
| 8 | ALL | RS4;11 | ATCC | RPMI1640 + 10% FBS |
| 9 | ALL | SUP-B15 | ATCC | RPMI1640 + 10% FBS |
| 10 | AML | HL-60 | SIBS | Ham's F12K + 10% FBS |
| 11 | AML | Kasumi-1 | ATCC | RPMI1640 + 10% FBS |
| 12 | AML | ML-2 | DSMZ | RPMI1640 + 10% FBS |
| 13 | AML | MOLM-13 | DSMZ | RPMI1640 + 10% FBS |
| 14 | AML | MOLM-16 | DSMZ | RPMI1640 + 10% FBS |
| 15 | AML | MV-4-11 | ATCC | RPMI1640 + 10% FBS |
| 16 | AML | NB4 | DSMZ | RPMI1640 + 10% FBS |
| 17 | AML | THP-1 | SIBS | Ham's F12K + 10% FBS |
| 18 | AML | Reh | SIBS | Ham's F12K + 10% FBS |
| 19 | AML | TF-1 | SIBS | RPMI1640 + 10% FBS + 2 ng/ml GM-CSF |
| 20 | CLL | EHEB | DSMZ | RPMI1640 + 10% FBS |
| 21 | CLL | JVM-13 | DSMZ | RPMI1640 + 10% FBS |
| 22 | CLL | JVM-2 | DSMZ | RPMI1640 + 10% FBS |
| 23 | CLL | JVM-3 | SIBS | RPMI1640 + 10% FBS |
| 24 | CLL | MEC-1 | DSMZ | RPMI1640 + 10% FBS |
| 25 | CLL | MEC-2 | DSMZ | RPMI1640 + 10% FBS |
| 26 | CML | K-562 | SIBS | Ham's F12K + 10% FBS |
| 27 | CML | KU812 | ATCC | RPMI1640 + 10% FBS |
| 28 | CML | MEG-01 | ATCC | RPMI1640 + 10% FBS |

ATCC—USA;
DSMZ—Germany;
SIBS—China
*applicable for all cell lines/all experiments All cells were cultured in the media supplemented with 10% FBS, at 37° C., under 5% $CO_2$ and 95% humidity. Culture media were purchased from GIBCO or Sigma, USA.

TABLE 5

Abbreviations used in this study example

| Abbreviations | Full-text & descriptions |
|---|---|
| ALL | Acute Lymphoblastic Leukemia |
| AML | Acute Myeloid Leukemia |
| CLL | Chronic Lymphocytic Leukemia |
| CML | Chronic Myeloid Leukemia |
| FBS | Fetal Bovine Serum |
| DMSO | Dimethyl Sulfoxide |
| PBS | Phosphate Buffered Saline |
| USA | United States of America |
| ATCC | American Type Culture Collection |
| DSMZ | Deutsche Sammlung von Mikroorganismen and Zellkulturen |
| SIBS | Shanghai Institutes of Biological Sciences |
| FU | Fluorescence Unit |

TABLE 6

Reagents

| Name | Manufacturer | Cat. No |
|---|---|---|
| Ham's F12K | GIBCO | 21127-022 |
| RPMI 1640 | Hyclone | SH30809.01B |
| IMDM | Hyclone | SH30228.01B |
| FBS | GIBCO | 10099-141 |
| Trypsin | AMRESCO | 458 |
| PrestoBlue | Life Technologies | A-13262 |
| PBS | Crownbio | JJL-2014 |

Preparation of Test Solutions:

The "HES 130/0.4" used in this study was a 10 g sample from Lot #17123722 provided by Fresenius Kabi Austria GmbH. Prior to use it was stored at ambient temperature. It was characterized as follows:

TABLE 7

| Test parameter | Measured properties of batch "HES 130/0.4" used in example 2 |
|---|---|
| Appearance | Solid |
| Colour | white |
| Absorption 400 nm/1 cm | 0.006 |
| Mw* | 128,100 Da |
| Mw* of the 10% smallest fraction | 24.805 Da |
| Mw* of the 10% largest fraction | 288.038 Da |
| MS | 0.4 |
| C2/C6 | 9.7 |

*to determine the Mw values the method according to Sommermeyer, i.e. the dn/dc value of 0.135 was used.

An appropriate amount was dissolved to prepare a stock solution of 200 mg/ml (20%) using the respective cell medium, by providing an initial amount of the medium in a suitable container, carefully adding the calculated amount of HES under stirring to the serum-free medium, which took 5-20 min to obtain a clear solution, and finally adding the remaining amount of medium to adjust to the desired concentration (20 mg/ml). This stock solution was sterilized by filtering with a 0.22 μm pore size device and used immediately. The solution was prepared freshly prior to usage. All HES and reference working solutions were prepared freshly.

The cisplatin used in this study was purchased as a powder from Lot #212029CF from Nanjing Zhiyao, China, with an expiry date of July 2016. Prior to use it was stored at room temperature. Its molecular weight was determined to be 300.05 Da.

Cisplatin was dissolved in PBS to produce a stock solution at the concentration of 2.0 mM.

Equipments

EnVision Multi Label Reader 2104-0010A, Perkin Elmer (USA), Equip ID: BMRP004; Countstar, Inno-Alliance Biotech (USA), Equip ID: BANA011; Forma Series II Water Jacket $CO_2$ Incubator, Thermo Scientific (USA), Equip ID: BINC040/BINC045/BINC046; Biological safety Cabinet, Thermo Scientific, (USA), Equip ID: BBSC021/BBSC022/BBSC024/BBSC025; Inverted Microscope, Olympus CKX41SF (Japan), Equip ID: BMIC020.

Determination of the Half Maximal Inhibition Concentration $IC_{50}$

Cells were harvested during the logarithmic growth period and counted using the commercially available cell counting device Countstar. The cell concentrations were adjusted to $3.33 \times 10^4$ cells/ml with respective culture medium containing 20% FBS. 60 µl cell suspensions were added to two 96-well plates (A and B) with the final cell density of 2×10³ cells/well.

Performance of $T_0$ Reading on the Next Day to Monitor the Cell Quality by Testing the Growth Rate of Each Cell Line.

In each well of the plate for $T_0$ reading 60 µl serum free culture medium was added. The plates were incubated overnight in a humidified incubator at 37° C. with 5% $CO_2$ Plates were equilibrated at room temperature for approximately 30 minutes. Thereafter 13 µl PrestoBlue® Reagent (10× solution) purchased from Life Technologies was given directly onto cells in culture medium. Contents were mixed for 2 minutes on an orbital shaker. The plate was then incubated at room temperature for 30 minutes until fluorescence ($T_0$) could be recorded using EnVision Multi Label Reader (Excitation: 540-570 nm/Emission: 580-610 nm).

Test Reading Plates

The plate was incubated overnight in the humidified incubator at 37° C. with 5% $CO_2$. HES was dissolved in culture medium without FBS (see above) at the concentration of 200 mg/ml (20%) to form 2×solution and sterilized by filtering with a 0.22 µm pore size device. The 2×solution of HES was diluted with culture medium (2-fold) to reach 9 dose levels: 10, 5, 2.5, 1.25, 0.63, 0.31, 0.16, 0.08, 0.04% or 100, 50, 25, 12.5, 6.25, 3.13, 1.56, 0.78, 0.39 mg/ml, respectively.

60 µl (2×) solution of "HES 130/0.4" was dispensed in each well (triplicate for each drug concentration) of the test plate.

The test plate was incubated for 72 h in a humidified incubator at 37° C. with 5% $CO_2$, and then measured by means of PrestoBlue assay. Thereafter 13 µl PrestoBlue® Reagent (10× solution) was given directly onto cells in culture medium. Contents were mixed for 2 minutes on an orbital shaker. The plate was then incubated at room temperature for 30 minutes until fluorescence (T0) could be recorded using EnVision Multi Label Reader (Excitation: 540-570 nm/Emission: 580-610 nm).

Data Analysis

The data were displayed graphically using GraphPad Prism 5.0.

In order to calculate $IC_{50}$, a dose-response curve was fitted using nonlinear regression model with a sigmoidal dose response. The formula of surviving rate is shown below, and the $IC_{50}$ was automatically produced by GraphPad Prism 5.0.

The surviving rate (%)=($FU_{Test\ item}$−$FU_{Medium\ control}$)/($FU_{None\ treated}$−$FU_{Medium\ control}$)×100%.

FU: Fluorescence unit

Table 8 demonstrates how the application of HES inhibits viability, or cell proliferation rates of all types of hematological neoplasmic cells, be it AML; ALL; CML or CLL type cells.

TABLE 8

| | | Results | | | |
|---|---|---|---|---|---|
| | | HES | | Cisplatin | |
| No. | Cell Line | $IC_{50}$ (mg/ml) | Max-inhibition (%) | $IC_{50}$ (mg/ml) | Max-inhibition (%) |
| 1 | CCRF-SB | 40.75 | 90 | 0.10 | 100 |
| 2 | Jurkat | 29.05 | 100 | 0.20 | 100 |
| 3 | MHH-CALL-2 | 42.07 | 88 | 0.14 | 100 |
| 4 | Molt-4 | 41.64 | 92 | 0.15 | 100 |

TABLE 8-continued

| | | Results | | | |
|---|---|---|---|---|---|
| | | HES | | Cisplatin | |
| No. | Cell Line | $IC_{50}$ (mg/ml) | Max-inhibition (%) | $IC_{50}$ (mg/ml) | Max-inhibition (%) |
| 5 | MUTZ-5 | 43.93 | 83 | 0.19 | 100 |
| 6 | NALM 6 | 32.98 | 100 | 0.24 | 100 |
| 7 | PEER IE6 | 56.79 | 68 | 3.73 | 100 |
| 8 | RS4;11 | 28.53 | 100 | 0.05 | 100 |
| 9 | SUP-B15 | 41.54 | 86 | 0.45 | 100 |
| 10 | HL-60 | 39.47 | 96 | 0.45 | 100 |
| 11 | Kasumi-1 | 30.41 | 100 | 0.78 | 100 |
| 12 | ML-2 | 34.22 | 90 | 0.35 | 100 |
| 13 | MOLM-13 | 42.43 | 91 | 0.34 | 100 |
| 14 | MOLM-16 | 35.39 | 100 | 0.65 | 100 |
| 15 | MV-4-11 | 44.63 | 93 | 0.16 | 100 |
| 16 | NB4 | 53.70 | 80 | 0.14 | 100 |
| 17 | THP-1 | 44.62 | 89 | 0.64 | 100 |
| 18 | Reh | 42.87 | 93 | 0.17 | 100 |
| 19 | TF-1 | 40.77 | 76 | 1.72 | 100 |
| 20 | EHEB | 33.40 | 100 | 0.49 | 100 |
| 21 | JVM-13 | 39.70 | 92 | 0.18 | 100 |
| 22 | JVM-2 | 40.47 | 94 | 0.18 | 100 |
| 23 | JVM-3 | 45.59 | 79 | 0.27 | 100 |
| 24 | MEC-1 | 57.16 | 63 | 1.15 | 100 |
| 25 | MEC-2 | 61.23 | 60 | 1.67 | 100 |
| 26 | K-562 | 73.23 | 62 | 1.29 | 100 |
| 27 | KU812 | 28.72 | 100 | 0.25 | 100 |
| 28 | MEG-01 | 40.45 | 93 | 0.83 | 100 |

A total of 28 leukemia cell lines were tested in this study and the compound hydroxyethyl starch (HES) 130/0.4 had a clearly inhibiting effect on all cell lines of the different leukemia types: acute lymphoblastic leukemia, acute myeloid leukemia, chronic lymphocytic leukemia and chronic myeloid leukemia.

Figure 3:
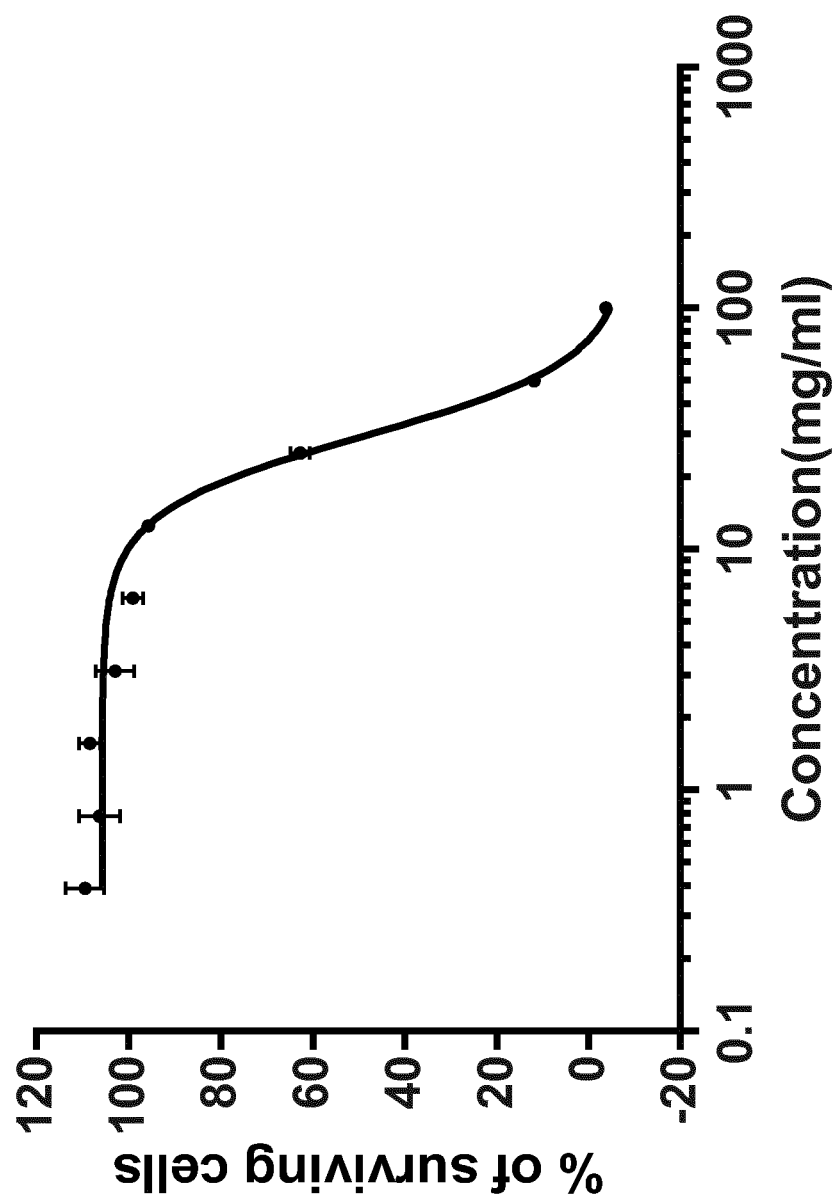
In FIGS. 3 to 6 the inhibitory effect of hydroxyethyl starch ("HES 130/0.4" as characterized in table 7) on different hematological neoplastic cells is shown. Values on the Y-axis indicate the number of surviving cells in % determined with the viability test based on the use of Prestoblue® after treatment with the tested hydroxyalkyl starch "HES 130/0.4" (at 9 different concentrations). Values on the X-axis indicate the different HES concentrations in mg/ml tested.
Figure 4:
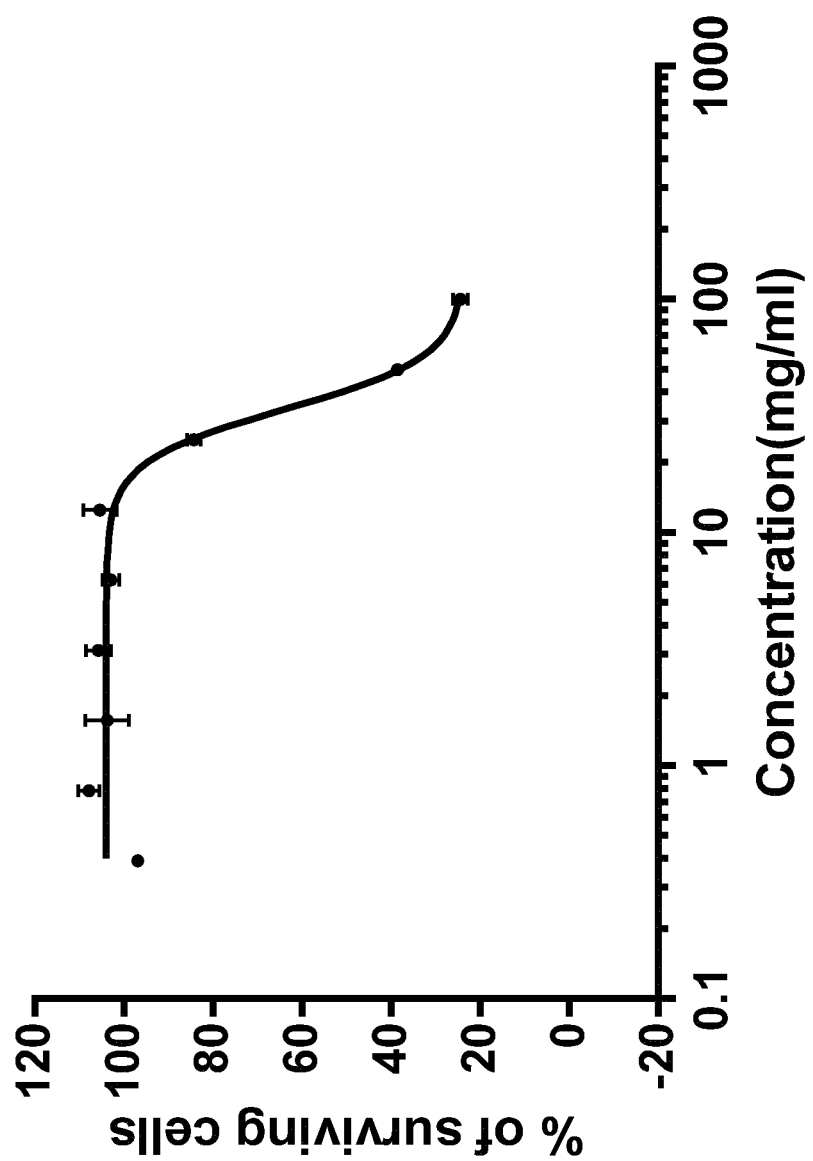
Figure 5:
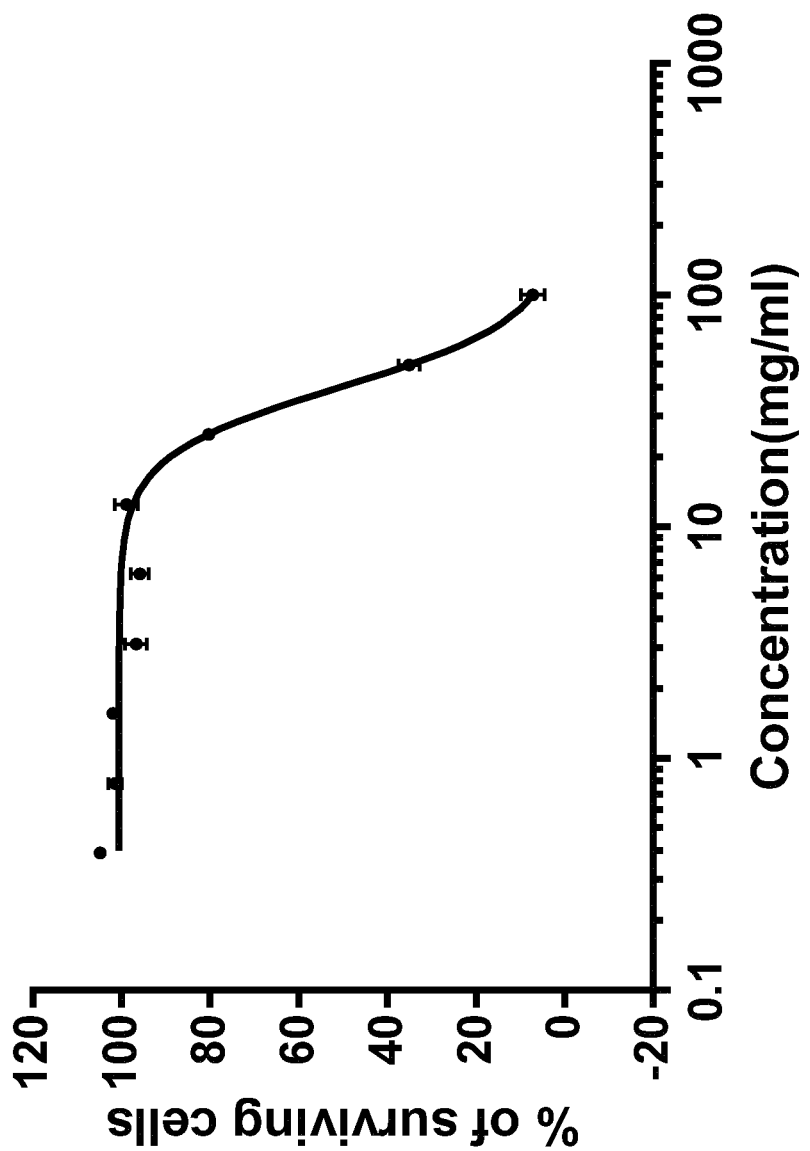
Figure 6:
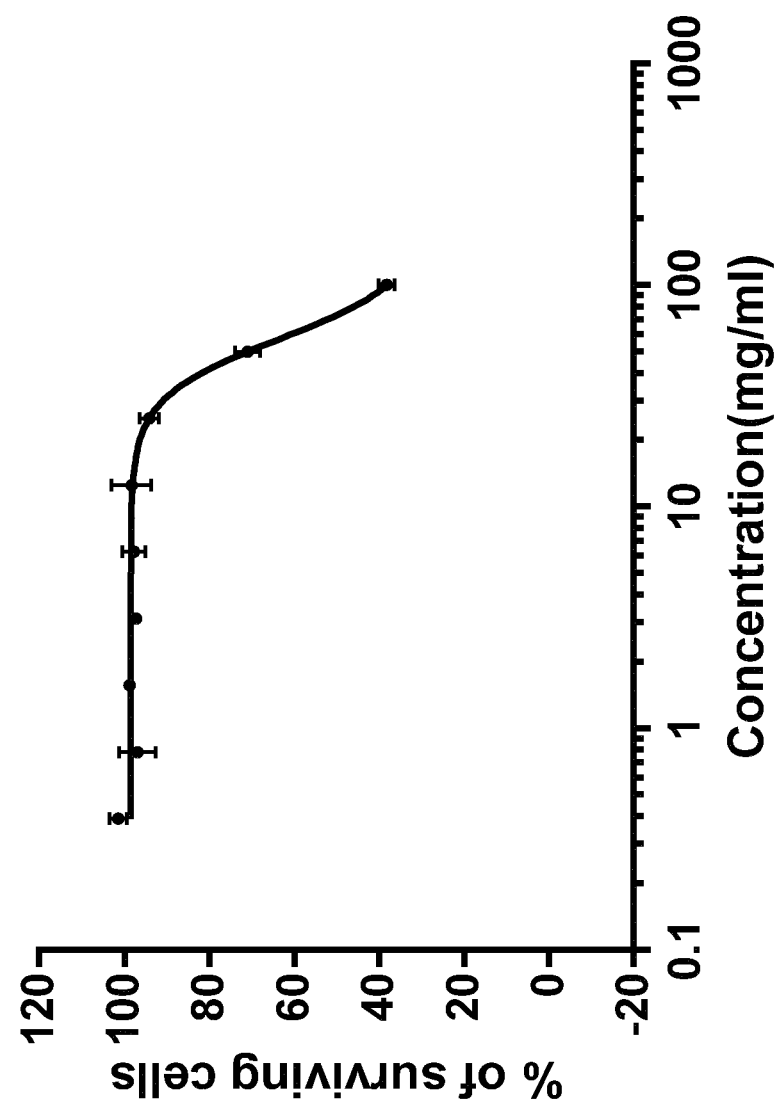

Notably, HES 130/0.4 was most potent on Jurkat cells (as shown in FIG. 3), but still a remarkable effect on the other 27 cell lines could be demonstrated as well. The results of this study suggest a correlation between potency and efficacy. The more sensitive cell lines presented higher maximum inhibition values when treated with HES than the less sensitive cells.

The invention claimed is:

1. A method of treating a subject who has a hematological neoplasm, the method comprising administering a therapeutically effective amount of hydroxyethyl starch (HES) to the subject;
    wherein the HES has a mean molecular weight (MW) above 20 and below 1300 kDa and a molar substitution (MS) in the range of from 0.1 to 1.5.

2. The method of claim 1, wherein the hematological neoplasm is leukemia or lymphoma.

3. The method of claim 1, wherein the treatment comprises at least one of reducing the growth or proliferation of hematological neoplastic cells or inhibiting hematological neoplastic cell infiltration into peripheral organs.

4. The method of claim 1, wherein the HES is administered as a first compound, either before or after administration of a second therapeutically effective compound.

5. The method of claim 4, wherein the second compound is a cytostatica, a biological with anti-cancer activity, or a hormone with anti-cancer activity.

6. The method of claim 4, wherein the second compound is selected from the group consisting of a cytostatica and a biological with anti-cancer activity.

7. The method of claim 4, wherein the second compound is a cytostatica.

8. The method of claim 5, wherein the cytostatica is an alkylating agent, an alkyl sulfonate, and antimetabolite, an anti-tumor antibiotic, a topoisomerase inhibitor, a differentiating agent selected from the group consisting of tretinoin, bexarotene, and arsenic trioxide, a mitotic inhibitor, a tyrosine kinase inhibitor selected from the group consisting of imatinib, dasatinib, ponatinib, ibrutinib, bosutinib, and nilotinib, a proteasome inhibitor or plerixafor.

9. The method of claim 4, wherein the second compound is a biological with anti-cancer activity.

10. The method of claim 5, wherein the biological with anti-cancer activity consists of an antibody tyrosine kinase inhibitor, a monoclonal antibody or an immunomodulating drug selected from the group consisting of thalidomide, lenalidomide, and pomalidomide.

11. The method of claim 1, wherein the hematological neoplasm is selected from the group consisting of myeloproliferative neoplasms, myeloid and lymphoid neoplasms associated with eosinophilia and abnormalities of platelet-derived growth factor receptor alpha (PDGFRA), platelet-derived growth factor receptor beta (PDGFRB), or fibroblast growth factor receptor-1 (FGFR1), myelodisplastic/myeloproliferative neoplasms (MDS/MPN), myelodisplastic syndromes, acute myeloid leukemia (AML), acute leukemia of ambiguous lineage, precursor lymphoid neoplasms, mature B-cell neoplasms, mature T-cell and NK-cell neoplasms, Hodgkin lymphoma, histiocytic and dendritic cell neoplasms, and post transplantation lymphoproliferative disorders (PTLDs).

12. The method of claim 1, wherein the treatment comprises arresting the mitotic cycle of a hematological neoplasm cell.

13. The method of claim 8, wherein alkylating agent is cyclophosphamide.

14. The method of claim 1, wherein the HES is HES 130/0.4; HES 100/1.0/1.3; HES 200/0.5; HES 70/0.4/1.8; HES 70/0.5; HES 100/0.1/2.0 (with a mean molecular weight of 100 kDa, a molar substitution degree of 0.1 and a poly dispersity index (PDI) of 2.0); HES 100/0.1/2.0 (with a mean molecular weight of 130 kDa, a molar substitution degree of 0.1 and a PDI of 2.0); HES 100/0.7/1.3; HES 100/1.0/1.1; HES 150/0.7/1.3 (with a mean molecular weight of 150 kDa, a molar substitution degree of 0.7 and a PDI of 1.3); HES 150/1.0/1.3 (with a mean molecular weight of 150 kDa, a molar substitution degree of 1.0 and a PDI of 1.3); HES 180/0.4; HES 200/0.5; HES 250/0.45; HES 300/1.0/1.3; HES with a mean molecular weight of 300 kDa, HES 450/0.7; HES with a mean molecular weight of 500 kDa, a molar substitution degree of 0.28 and a C2/C6 ratio of 8.7; HES with a mean molecular weight of 500 kDa and a molar substitution degree MS between 0.25 and 0.5 and a C2/C6 ratio of 2 to below 8; HES with a mean molecular weight of 600 kDa and a molar substitution degree of 0.5; HES 700/0.5/2.5; HES 700/0.7; HES 700/0.7/2.0; HES 700/1.0/1.5; HES 700/1.3/1.5; HES 60/1.3/1.3; a HES with a mean molecular weight Mw of 1000 kDa and a substitution degree Ds between 4 and 10; and HES 70/0.55.

15. The method of claim 14, wherein the HES 130/0.4 has a molar substitution degree of 0.38-0.45, a mean molar substitution degree of 0.42, a C2/C6 ratio between 8.0 and 12.0, and a PDI between 1.7 and 2.3.

16. The method of claim 10, where the antibody tyrosine kinase inhibitor is cetuximab, bevacizumab, panitumumab, or trastuzumab.

* * * * *